US012799148B2

(12) United States Patent
Boettger et al.

(10) Patent No.: US 12,799,148 B2
(45) Date of Patent: Nov. 17, 2026

(54) PROCESS FOR PRODUCING 1,1-GPM- AND/OR 1,6-GPS-ENRICHED ISOMALT COMPOSITIONS

(71) Applicant: SÜDZUCKER AG, Mannheim (DE)

(72) Inventors: Christoph Boettger, Battenberg (DE); Ralph Cartarius, Offenau (DE); Hanspeter Degelmann, Bamberg (DE); Holger Janßen, Nieder-Flörsheim (DE); Markwart Kunz, Braunschweig (DE); Julia Sünner, Neustadt (DE); Rolf Wallot, Quirnheim (DE)

(73) Assignee: SÜDZUCKER AG, Mannheim (DE)

( * ) Notice: Subject to any disclaimer, the term of this patent is extended or adjusted under 35 U.S.C. 154(b) by 457 days.

(21) Appl. No.: 18/555,206

(22) PCT Filed: Apr. 13, 2022

(86) PCT No.: PCT/EP2022/059965
§ 371 (c)(1),
(2) Date: Oct. 12, 2023

(87) PCT Pub. No.: WO2022/219094
PCT Pub. Date: Oct. 20, 2022

(65) Prior Publication Data

US 2024/0199674 A1 Jun. 20, 2024

(30) Foreign Application Priority Data

Apr. 15, 2021 (EP) .................................... 21168625

(51) Int. Cl.
*C07H 1/06* (2006.01)
*A23L 27/30* (2016.01)
*C07H 15/04* (2006.01)

(52) U.S. Cl.
CPC ................ *C07H 1/06* (2013.01); *A23L 27/34* (2016.08); *C07H 15/04* (2013.01)

(58) Field of Classification Search
CPC C07H 1/06; C07H 15/04; A23L 27/34; A23L 29/37
See application file for complete search history.

(56) References Cited

U.S. PATENT DOCUMENTS 4,117,173 A 9/1978 Schiweck et al.
6,414,138 B1 7/2002 Degelmann et al.
6,555,146 B1 * 4/2003 Rapp ........................ A23G 3/38 426/549
6,746,541 B2 * 6/2004 Ueno ...................... A23L 27/34 127/29
2003/0175396 A1 9/2003 Rapp et al.

FOREIGN PATENT DOCUMENTS

| | | | |
|---|---|---|---|
| CN | 101759729 | A | 6/2010 |
| CN | 101781341 | A | 7/2010 |
| DE | 2520173 | A1 | 12/1976 |
| EP | 0625578 | A | 11/1994 |
| EP | 0859006 | B2 | 8/1998 |
| EP | 1013175 | A1 | 6/2000 |
| WO | 1997008958 | A1 | 3/1997 |

OTHER PUBLICATIONS

Lovette et al., Ind. Eng. Chem. Res., 2008, 47, p. 9812-9833. (Year: 2008).*
Chinese Office Action issued by the China National Intellectual Property Administration in connection with International Application No. 2022800278857, dated Jun. 14, 2025.
International Preliminary Report on Patentability issued by the International Bureau of WIPO in connection with International Application No. PCT/EP2022/059965, dated Oct. 12, 2023.
International Search Report and Written Opinion of the International Searching Authority issued in corresponding application PCT/EP2022/059965 mailed Aug. 3, 2022 (18 pages).
Bartens, "Carbohydrates in Industrial Synthesis", 3.2 Production of Isomalt", Proceedings of the Symposium of the Division of Carbohydrate Chemistry of the American Chemical Society", 1992, Bartens, DE, XP009530270, ISBN: 978-3-87040-052-1, pp. 48-55.
Japanese Office Action issued by the Japan Patent Office in connection with International Application No. 2023-562845, dated Dec. 10, 2025.

* cited by examiner

*Primary Examiner* — Jonathan S Lau
(74) *Attorney, Agent, or Firm* — Carter, DeLuca & Farrell LLP; George Likourezos

(57) ABSTRACT

The present invention relates to a method for producing 1-O-α-D-glucopyranosyl-D-mannitol- (hereinafter referred to as 1,1-GPM) and/or 6-O-α-D-glucopyranosyl-D-sorbitol- (hereinafter referred to as 1,6-GPS) enriched isomalt compositions from isomalt-containing solutions, i.e. solutions containing hydrogenated isomaltulose, 1,1-GPM- and/or 1,6-GPS-enriched isomalt compositions from isomalt-containing solutions produced by the method according to the invention, as well as the use of these 1,1-GPM- and/or 1,6-GPS-enriched isomalt compositions.

41 Claims, 6 Drawing Sheets

Figure 1:
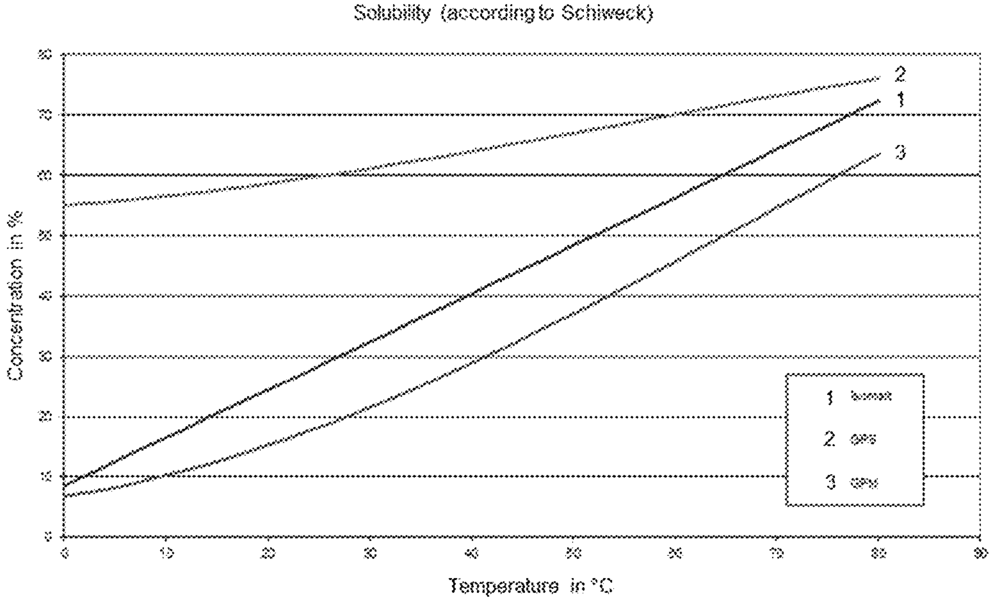

Figure 2
Figure 2 A
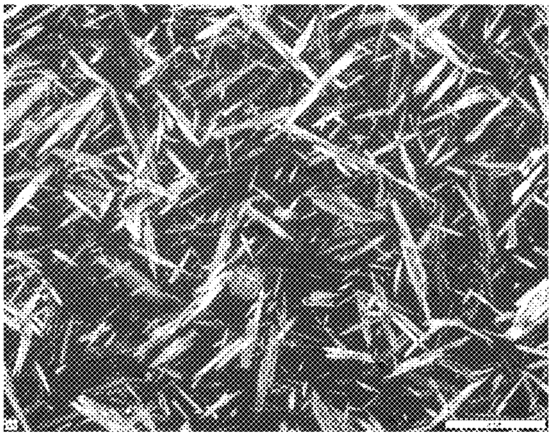
Figure 2 B
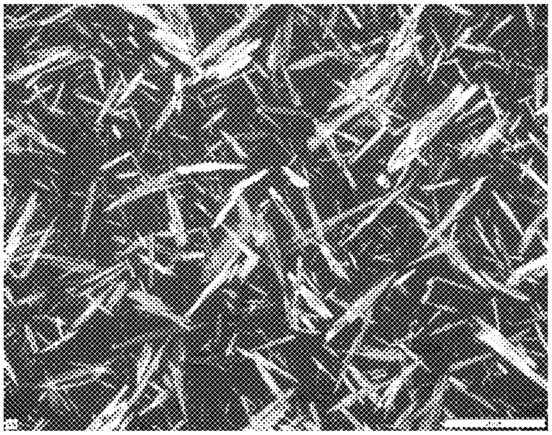
Figure 2 C
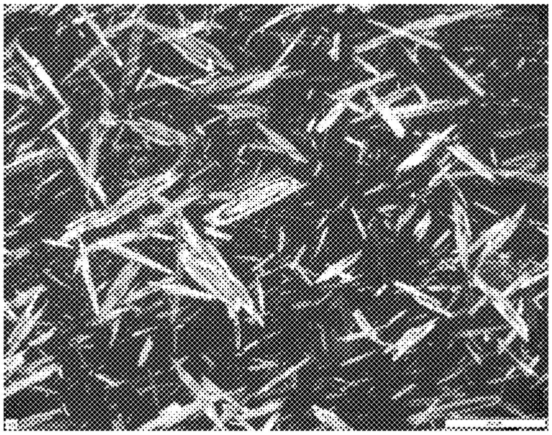
Figure 2 D
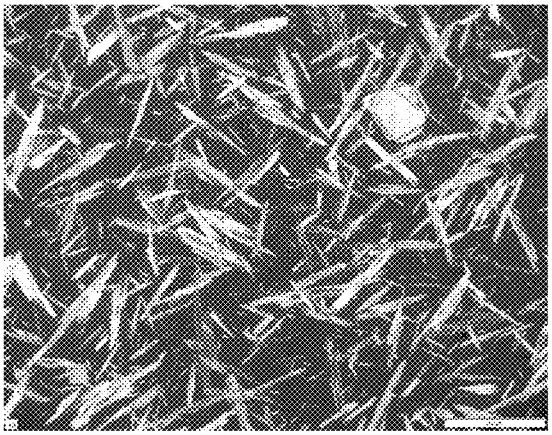

Figure 3
Figure 3 A
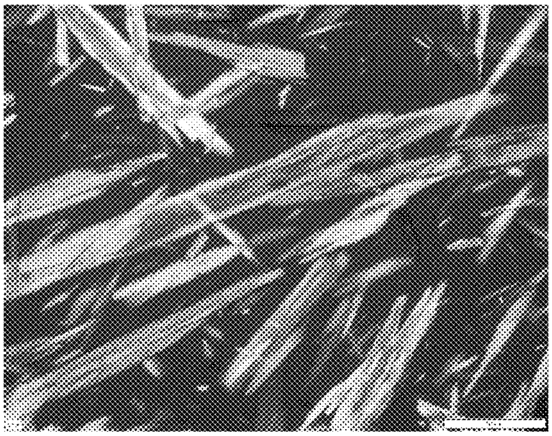
Figure 3 B
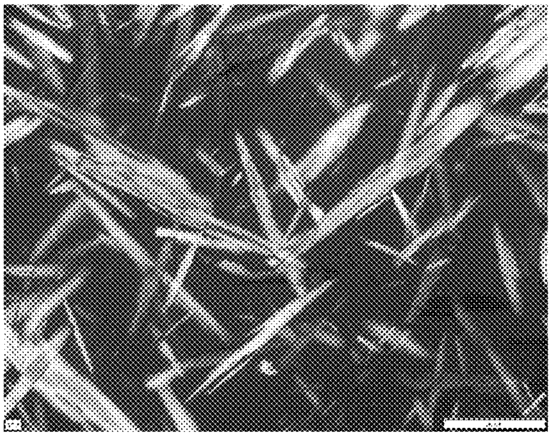
Figure 3 C
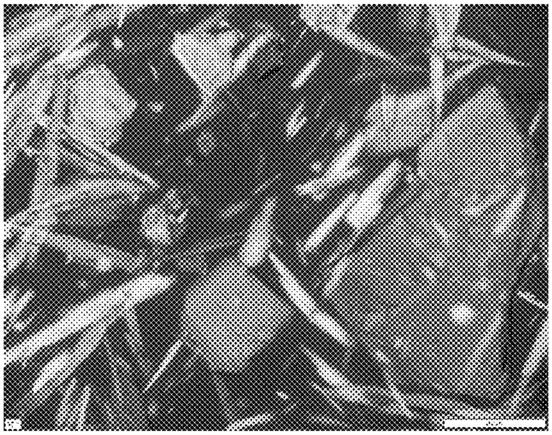
Figure 3 D
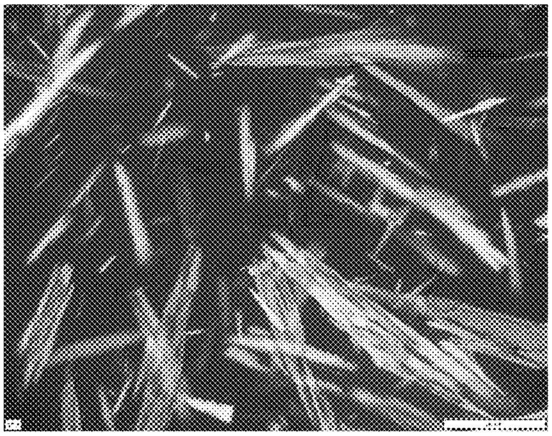

Figure 4
Figure 4 A
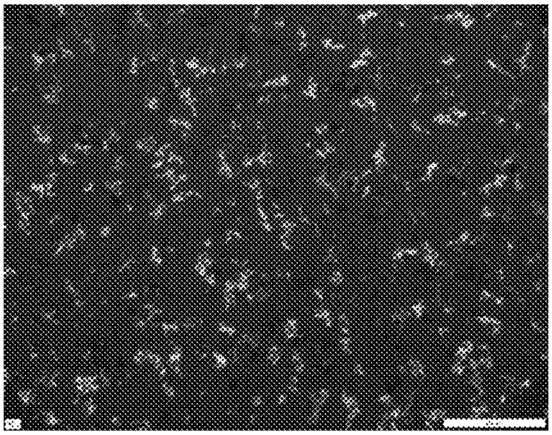
Figure 4 B
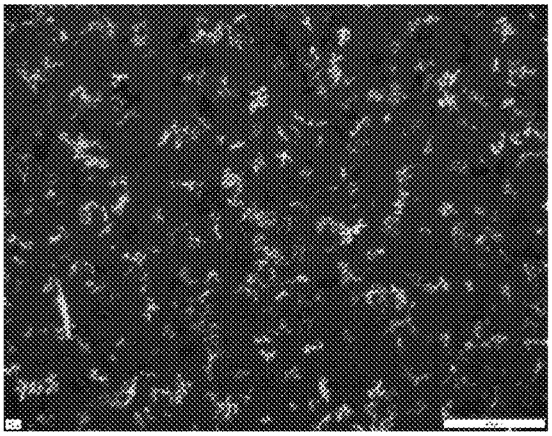
Figure 4 C
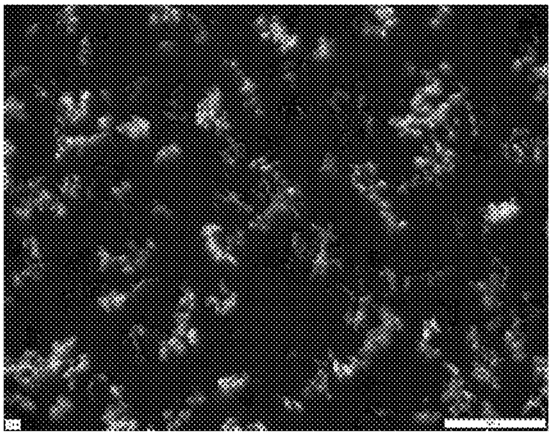
Figure 4 D
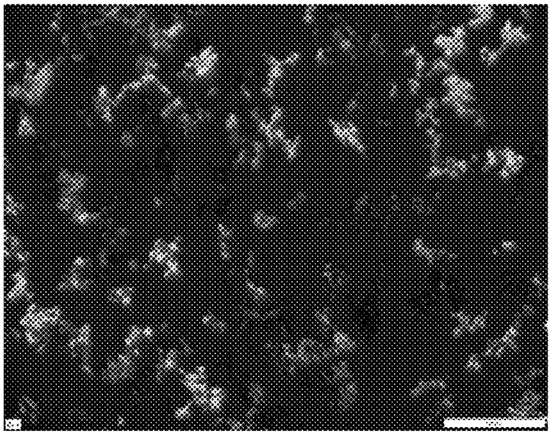

Figure 5
Figure 5 A
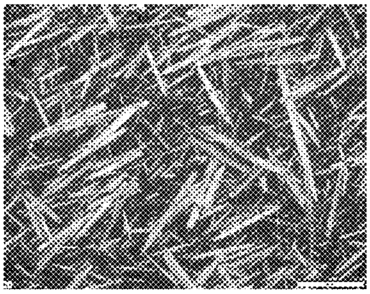
Figure 5 B
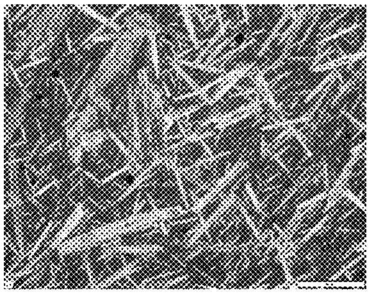
Figure 5 C
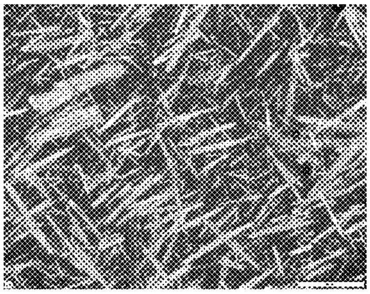
Figure 5 D
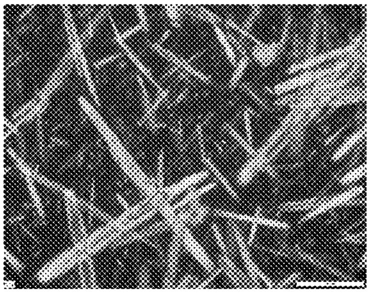
Figure 5 E
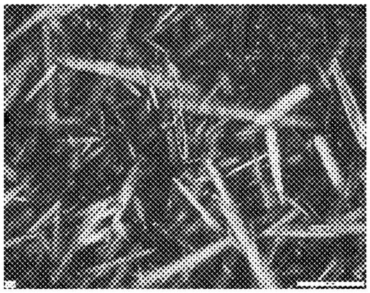
Figure 5 F
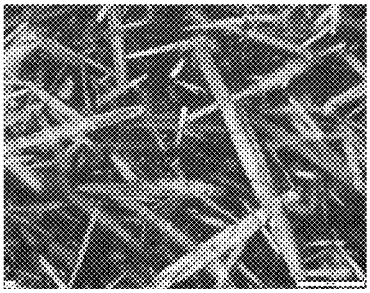

Figure 6
Figure 6 A
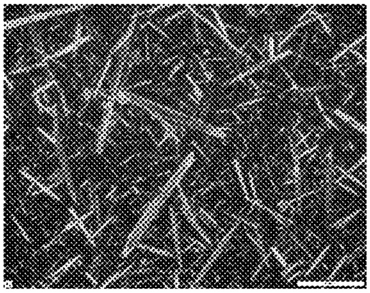
Figure 6 B
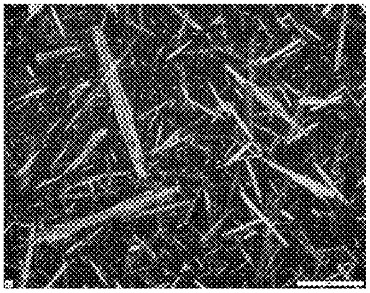
Figure 6 C
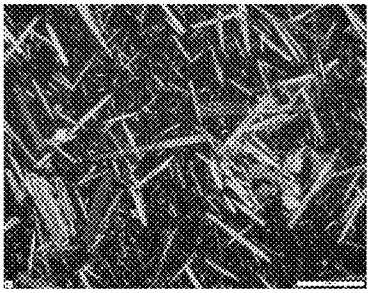
Figure 6 D
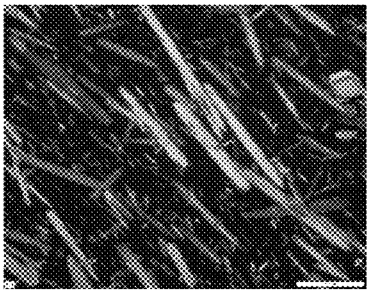
Figure 6 E
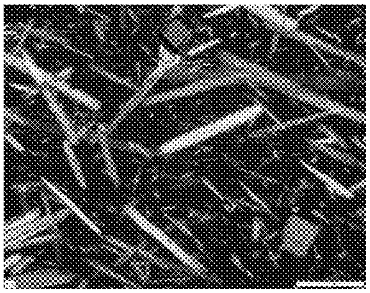
Figure 6 F
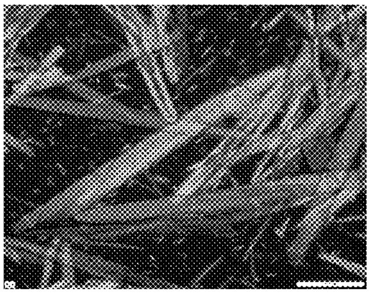

PROCESS FOR PRODUCING 1,1-GPM- AND/OR 1,6-GPS-ENRICHED ISOMALT COMPOSITIONS

CROSS REFERENCE TO RELATED APPLICATIONS

The present application is a national stage application of International Application No. PCT/EP2022/059965, filed Apr. 13, 2022, which claims priority to European Patent Application No. 21168625.8, filed Apr. 15, 2021, the entire contents of which are incorporated herein by reference in their entirety.

The present invention relates to a method for producing 1-O-α-D-glucopyranosyl-D-mannitol- (hereinafter referred to as 1,1-GPM) and/or 6-O-α-D-glucopyranosyl-D-sorbitol- (hereinafter referred to as 1,6-GPS) enriched isomalt compositions from isomalt-containing solutions, i.e. solutions containing hydrogenated isomaltulose, 1,1-GPM- and/or 1,6-GPS-enriched isomalt compositions from isomalt-containing solutions produced by the method according to the invention, as well as the use of these 1,1-GPM- and/or 1,6-GPS-enriched isomalt compositions.

Isomalt (hydrogenated isomaltulose or hydrogenated palatinose) is a sugar substitute having as major components 1,1-GPM and 1,6-GPS, which is advantageous due to its acariogenicity, low calorific value and diabetic suitability. 1,1-GPM- and/or 1,6-GPS-enriched isomalt compositions from an isomalt-containing solution are more suitable for a plurality of applications than products having an almost equimolar ratio of 1,1-GPM to 1,6-GPS.

DE 25 20 173 A1 relates to a method for producing 1,6-GPS and 1,1-GPM from isomaltulose and its use as a sugar substitute.

EP 0 625 578 A1 discloses the production of isomalt and its use as a sweetener in luxury food and food products.

EP 0 859 006 B2 and WO 1997/008958 A1 relate to methods for producing 1,6-GPS-enriched and 1,1-GPM-enriched mixtures, 1,6-GPS and 1,1-GPM in pure form and the use thereof.

Such isomalt compositions are used in many products, for example in the luxury food and food sector. The potentially very wide range of applications of such compositions requires, depending on the end product, compositions having different amounts of 1,1-GPM and 1,6-GPS, in particular also those which are 1,1-GPM- or 1,6-GPS-enriched.

However, a crystallisation process for producing such 1,1-GPM- and/or 1,6-GPS-enriched isomalt compositions from an isomalt-containing solution, as well as 1,6-GPS and 1,1-GPM in pure form, which permits simple, safe and efficient, in particular cost- and/or energy-efficient, production, is currently not known. Accordingly, there is a need for methods that enable isomalt compositions to be obtained from an isomalt-containing solution that are enriched compared to the contents of 1,1-GPM and/or 1,6-GPS in the isomalt-containing solutions present as initial solution.

The invention is therefore based on the technical problem of providing a crystallisation process for the production of 1,1-GPM- and/or 1,6-GPS-enriched isomalt compositions from an isomalt-containing solution, which is simple and safe to carry out and which results in 1,1-GPM- and/or 1,6-GPS-enriched isomalt compositions from an isomalt-containing solution in high yield and reproducibly.

The present invention solves the technical problem by providing a method for producing 1,1-GPM- and/or 1,6-GPS-enriched isomalt compositions from an isomalt-containing solution, characterised in that a) an isomalt-containing solution is provided, wherein the isomalt-containing solution has 65 to 90 wt. %, in particular 70 to 85 wt. %, isomalt (each based on the total weight of the isomalt-containing solution);
b) the isomalt-containing solution provided in method step a) is subjected to flash evaporation in a reactor for crystal nucleation to obtain a first isomalt-containing suspension comprising a first crystalline phase and a first liquid phase;
c) the first isomalt-containing suspension obtained in method step b) is subjected to a crystallisation process whereby a second isomalt-containing suspension comprising a second crystalline phase and a second liquid phase is obtained, wherein the second crystalline phase is 1,1-GPM-enriched and the second liquid phase is 1,6-GPS-enriched;
d) the 1,1-GPM-enriched second crystalline phase of the second isomalt-containing suspension of method step c) is separated from the 1,6-GPS-enriched second liquid phase; and
e) 1,1-GPM- and/or 1,6-GPS-enriched isomalt compositions are obtained.

The invention therefore starts from an isomalt-containing solution as initial solution, which is provided in method step a) and is subjected to a method, in particular using method steps b), c), d) and e), for providing two different phases, namely a second crystalline phase and a second liquid phase, wherein the second crystalline phase has a higher 1,1-GPM-content than the isomalt-containing solution used in method step a) and the second liquid phase has a higher 1,6 GPM-content than the isomalt-containing solution used in method step a). The present invention therefore enables a separation of the isomalt-containing solution into two phases with phase-specific enrichment of the components present in the isomalt-containing solution used as initial solution, 1,1-GPM in the second crystalline phase and 1,6-GPS in the second liquid phase and, according to the invention, provides 1,1-GPM- and 1,6-GPS-enriched phases and compositions which are specifically enriched with respect to the 1,1-GPM- and 1,6-GPS-content compared to the respective 1,1-GPM- and 1,6-GPS-content in the initial solution and are particularly suitable for certain applications.

Thus, according to the invention, by going through the method steps b) and c), two phases are obtained, namely a second crystalline phase and a second liquid phase, wherein in the second crystalline 1,1-GPM-enriched phase the 1,1-GPM-content is higher than the 1,1-GPM-content in the isomalt-containing solution used in method step a) and the 1,6-GPS-content being lowered, and in the second liquid 1,6-GPS-enriched phase the 1,1-GPM-content being lowered than the 1,1-GPM-content of the isomalt-containing solution used in method step a) and the 1,6-GPS-content being increased. By carrying out method steps d) and e), 1,1-GPM- and 1,6-GPS-enriched isomalt-containing compositions are obtained, i.e. a composition which is characterised by a higher content of 1,1-GPM compared to the isomalt-containing solution provided in method step a) and also a further composition which is characterised by a higher content of 1,6-GPS compared to the isomalt-containing solution provided in method step a).

Accordingly, the invention provides a method for producing 1,1-GPM- and/or 1,6-GPS-enriched isomalt compositions from an isomalt-containing solution, wherein an isomalt-containing solution, i.e. a solution containing an isomalt-containing mixture, is provided in a method step a) and in a method step b) flash evaporation in a reactor, in particular a nucleator, effects induced crystal nucleation, in the course of which crystal nucleation and crystallisation beginning at these crystal nuclei take place, obtaining a first isomalt-containing suspension, and in a method step c) by subsequent crystallisation in a reactor, in particular the same reactor or another reactor, in particular a crystalliser, a second isomalt-containing suspension comprising a second crystalline phase and a second liquid phase is obtained, wherein the second crystalline phase is enriched with 1,1-GPM and the second liquid phase is enriched with 1,6-GPS, and in a method step d) subsequently separating the 1,1-GPM-enriched phase from the 1,6-GPS-enriched phase to obtain in a method step e) subsequently a 1,1-GPM- and/or 1,6-GPS-enriched isomalt composition.

In an advantageous and particularly preferred manner, the method according to the invention results in a simple and efficient, in particular cost-efficient, process control. In particular, the preferably provided continuous process method in comparison with conventional crystal nucleation reactors, in particular slurry reactors, makes it possible to dispense with the interval-based, continuous addition of high-purity crystal nuclei which are time-consuming and cost-intensive to produce.

In an advantageous and particularly preferred manner, the method according to the invention results in a particularly homogeneous crystal nucleation, since local steps initiating the crystallisation, in particular inoculations, are dispensed with, since crystal nuclei are continuously formed independently in-operando, i.e. during the method according to the invention, i.e. during ongoing operation of the reactor. In an advantageous manner, the method according to the invention thus results in the avoidance of common technical problems, since the independent crystal nucleation takes place in the entire isomalt-containing solution used, whereas in common crystal nucleation reactors, in particular slurry reactors, the homogenisation of the suspension used, comprising seed crystals, crystallised solids and solvent, is often problematic, since the addition of crystal nuclei requires rapid mixing in order to avoid local concentration gradients and thus guarantee homogeneous crystal growth, wherein the destruction of already formed crystals often occurs. The invention relies on that the solubility of 1,1-GPM and 1,6-GPS differs in a solution, in particular in an aqueous solution, i.e. both components have different solubility equilibria, and consequently the two components accumulate and deplete to different extents in the crystalline and liquid phases respectively during flash evaporation and subsequent crystallisation. The solubility equilibria are temperature-dependent, wherein preferably the degree of enrichment of the two components can be specifically adjusted by controlling the shear and/or the process parameters, in particular pressure and/or temperature and/or the concentration of the components 1,1-GPM and/or 1,1-GPS in liquid phase.

The flash evaporation is preferably carried out at reduced pressure compared to atmospheric pressure, wherein the reduction of the absolute pressure leads to superheating of the liquid. Without being bound by theory, when the reduced absolute pressure is adjusted, the pressure drop spreads with a defined wave propagation in the reactor, especially nucleator, used for crystal nucleation, wherein this wave propagation is faster than the temperature adjustment of the liquid medium, which is slowed down by heat and mass transfers at the phase boundaries. Thus, a thermodynamic imbalance occurs and the superheat induced by pressure reduction is dissipated by energy transfer, in particular to boiling nuclei and/or to existing steam bubbles.

The reduction of the absolute pressure thus leads to the evaporation of a defined part of the solvent used, in particular water, whereby energy is withdrawn from the isomalt-containing solution used, i.e. the system cools down in a defined manner. The temperature dependence of the solubility equilibria of 1,1-GPM and 1,6-GPS enables, under the given process parameters and conditions, a defined crystal nucleation and a crystallisation starting at the formed crystal nuclei in a defined way, wherein the resulting crystal nuclei and crystals are enriched with 1,1-GPM and 1,6-GPS is enriched in the remaining liquid. Thus, the different solubility products of 1,1-GPM and/or 1,6-GPS are utilised by selective pressure reduction and temperature control in order to achieve an enrichment of the corresponding compounds in crystalline and liquid form. Accordingly, the flash evaporation carried out in method step b) leads to the formation of a first isomalt-containing suspension comprising a first crystalline phase and a first liquid phase, wherein 1,1-GPM is enriched in the first crystalline phase and 1,6-GPS is enriched in the first liquid phase.

The flash evaporation is preferably carried out until a sufficient enrichment of 1,1-GPM and/or 1,6-GPS is present in the obtained first crystalline phase and first liquid phase, in particular crystal nuclei and crystals grown thereon and formed therefrom comprising, in particular consisting of, 1,1-GPM are present in the first crystalline phase, in order to enable an efficient crystallisation process as well as homogeneous crystal growth.

The present invention also solves its underlying technical problem by providing intermediates obtained in the process performance as well as the obtained 1,1-GPM- and 1,6-GPS-enriched compositions. The present invention therefore also provides first and second crystalline and liquid phases as well as 1,1-GPM- and 1,6-GPS-enriched compositions.

The crystals contained in the second crystalline phase and the 1,1-GPM-enriched isomalt composition according to the invention are characterised by an advantageous morphology, in particular an advantageous length-to-width ratio of the crystals, in particular a small length-to-width ratio compared to conventionally crystallised products.

In a preferred embodiment according to the invention, the 1,1-GPM-enriched isomalt composition according to the invention, as well as the second crystalline phase obtained in method step c), has a length-to-width ratio of the crystals contained in each of them of from 7.0 to 10.5, in particular from 7.5 to 10.0, in particular from 7.5 to 9.0, in particular from 7.5 to 8.5, in particular from 8.0 (each mean value).

In a preferred embodiment according to the invention, the 1,1-GPM-enriched isomalt composition according to the invention, as well as the second crystalline phase obtained in method step c), has a length-to-width ratio of the crystals contained in each of them of from 6.5 to 10.0, in particular from 7.0 to 9.5, in particular from 7.5 to 9.0, in particular from 7.5 to 8.5, in particular from 7.8 (each median).

The 1,1-GPM-enriched isomalt compositions obtained according to the invention are advantageously readily separable from liquid components due to the special length-to-width ratio of the crystals contained therein. The length-to-width ratio according to the invention reduces crystal breakage and leads to a more homogeneous particle size distribution. This is advantageous as it is known that crystal breakage can lead to broader inhomogeneous particle size distributions with possibly even bimodal particle size distributions as well as clogging of the gap volume in the crystal cake, which worsens the separability of the crystals including the drainage of the crystal cake and thus reduces the product yield. The reduction of crystal breakage made possible according to the invention also has the advantage that the obtained products show no or only reduced dust formation after drying. The comparatively small and thus more spherical length-to-width ratio according to the invention also results in improved, in particular faster, sedimentation behaviour in centrifuges provided for separating the crystals, as well as better sieving with improved selectivity for the preferably obtained dried products. The length-to-width ratio according to the invention also reduces plug grain formation, i.e. the formation of crystal bodies characterised by a large length-to-width ratio, which clog separation screens due to their slender structure and thus also reduce production efficiency.

In an advantageous manner, the method according to the invention, in particular method step b), results in a particularly simple and effective crystal nucleation and/or enrichment of 1,1-GPM in a first crystalline phase and of 1,6-GPS in a first liquid phase.

The present invention provides that the flash evaporation in method step b) takes place in a reactor, in particular a nucleator. The present invention provides that the crystallisation process in method step c) takes place in a reactor, in particular a crystalliser.

In a particularly preferred embodiment, the present invention provides that the flash evaporation in method step b) takes place in a reactor, in particular a nucleator, and the crystallisation process in method step c) takes place in a reactor, in particular that the crystallisation process in method step c) takes place in the same reactor as the flash evaporation in method step b), in particular in the same nucleator.

In a particularly preferred embodiment, the present invention provides that the reactor used in method step b) is in particular a nucleator in which optionally method step c) can be carried out, whereby the nucleator is simultaneously a crystalliser.

In a particularly preferred embodiment, the present invention provides that the flash evaporation in method step b) takes place in a reactor, in particular a nucleator, and the crystallisation process in method step c) takes place in a reactor, in particular that the crystallisation process in method step c) takes place in a different reactor to the flash evaporation in method step b), in particular in a crystalliser.

Accordingly, in a particularly preferred embodiment, the present invention provides that method step b) and method step c) take place in the same reactor, in particular nucleator.

The present invention also provides in a particularly preferred embodiment that method step b) and method step c) each take place in a different reactor, namely method step b) in particular in a nucleator and method step c) in particular in a crystalliser.

In a preferred embodiment, the present invention provides that the flash evaporation in method step b) takes place in a reactor, in particular a nucleator, wherein the reactor, in particular the nucleator, has at least one agitator.

In a preferred embodiment, mechanical agitation is carried out during method step b), that is, preferably agitation, in particular stirring, of the isomalt-containing solution provided in method step a) is carried out during the flash evaporation.

In a particularly preferred embodiment, the mechanical agitation in method step b) is carried out by means of at least one agitator present in the reactor, in particular nucleator.

In an advantageous and preferred manner, the agitator preferably present in the nucleator ensures mechanical agitation, in particular particularly homogeneous mixing over the entire reactor contents of the isomalt-containing solution used in method step b) for flash evaporation according to the invention. This preferred homogeneous mixing caused by the agitator is achieved by shearing the isomalt-containing solution provided in method step a) and used in method step b). The control of the shearing in method step b), in conjunction with a control of the process parameters, in particular pressure and/or temperature and/or the concentration of the components 1,1-GPM and/or 1,6-GPS, in particular temperature reduction and increase of the dry matter content, helps to induce an advantageous rapid and homogeneous crystal nucleation, in particular at the preferably present rotor blade tips of the agitator, in order to distribute the thus generated crystal nuclei quickly and homogeneously over the entire reactor content, which ensures a uniform growth of the crystal nuclei and a controlled supersaturation reduction in the entire isomalt-containing solution.

Surprisingly, the preferably provided control of the shear and/or the process parameters, in particular pressure and/or temperature, leads to a homogeneous crystal nucleation advantageous according to the invention, wherein the shear caused by the preferably provided agitator advantageously avoids an uncontrolled crystal nucleation occurring only at high and local supersaturation, which spreads disadvantageously slowly and inhomogeneously from the point of origin over the rest of the isomalt-containing solution due to a lack of mixing.

The shear caused by the preferably used agitator of the nucleator used in method step b) can be adjusted by selecting various agitator parameters of the agitator, in particular selected from the agitator parameters rotational speed, in particular the blade tip speed, agitator geometry, in particular the extent of cavitation at the rotor blade tips generated thereby, as well as the number and/or shape and/or angle of the individual agitator blades, in particular rotor blades. In this way, the crystal nucleation, in particular the number of crystal nuclei, can be controlled, wherein the agitator is in particular a rotor-stator system.

Surprisingly, by controlling the shear and/or process parameters in method step b) in method step c), the size and particle size distribution of the forming crystals, in particular 1,1-GPM crystals, can be specifically influenced. Thus, according to the invention, in method step c) it is possible to subject the first isomalt-containing suspension comprising a first crystalline phase and a first liquid phase obtained in method step b) to a crystallisation process, whereby a second isomalt-containing suspension comprising a second crystalline phase and a second liquid phase is obtained, in particular a second isomalt-containing suspension comprising a homogeneous second crystalline phase and a second liquid phase, and wherein the number and size distribution of the 1,1-GPM crystals contained in the second crystalline phase of the second isomalt-containing suspension is specifically controlled by controlling the shear and/or the process parameters.

In a preferred embodiment, the at least one agitator is a rotor-stator system.

The present invention particularly preferably provides that the rotor-stator system comprises a rotor and a stator, in particular consists of a rotor and a stator.

The present invention particularly preferably provides that the rotor of the rotor-stator system is preferably a propeller stirrer, in particular a propeller stirrer with at least two rotor blades.

The present invention particularly preferably provides that the stator of the rotor-stator system is preferably a central tube.

The present invention particularly preferably provides that the rotor, in particular propeller stirrer is present in the stator, in particular central tube, in particular in such a way that free rotatability of the rotor is ensured.

The present invention particularly preferably provides that the rotor is present in the stator, in particular is present in such a way that, by means of the mechanical agitation preferably provided in method step b), the isomalt-containing solution provided according to the invention in method step a) can be permanently supplied on the side of the rotor blades and discharged on the opposite side of the rotor blades in order to ensure complete mixing of the reactor contents.

The present invention particularly preferably provides that the rotor blades of the propeller stirrer have a specific shape, in particular a rectangular shape, a trapezoidal shape, a double trapezoidal shape or a rectangular trapezoidal shape.

The present invention particularly preferably provides that the rotor of the rotor-stator system is a propeller stirrer, having at least 2 rotor blades, in particular 3, in particular 4, in particular 5, preferably 3 rotor blades.

The present invention particularly preferably provides that the rotor blades of the propeller stirrer, each starting from a central attachment point, are at an angle of 36 to 180°, in particular 45 to 120°, in particular 72 to 90°, preferably 72° (calculated from the centre of one rotor blade tip to the next) to the adjacent rotor blade.

The present invention particularly preferably provides that the rotor of the rotor-stator system is a propeller stirrer, comprising at least 2 rotor blades, in particular 3, in particular 4, in particular 5, preferably 3 rotor blades which, each starting from a central attachment point, are at an angle of 36 to 180°, in particular 45 to 120°, in particular 72 to 90°, preferably 72° (calculated from the centre of one rotor blade tip to the next) to the adjacent rotor blade.

The present invention particularly preferably provides that the rotor blades of the propeller stirrer are inclined about their longitudinal axis by 0°, in particular 1°, in particular 5°, in particular 10°, in particular 20°, in particular 30°, in particular 40°, in particular 45° (starting from rotor blades lying in a plane).

The present invention particularly preferably provides that the rotor of the rotor-stator system is a propeller stirrer having at least 2 rotor blades, in particular 3, in particular 4, in particular 5, preferably 3 rotor blades, each of which is at an angle of 36 to 180°, in particular 45 to 120°, in particular 72 to 90°, preferably 72° (calculated from the centre of one rotor blade tip to the next) to the adjacent rotor blade and are inclined about the longitudinal axis of the rotor blade by 0°, in particular 1°, in particular 5°, in particular 10°, in particular 20°, in particular 30°, in particular 40°, in particular 45° (starting from rotor blades lying in a plane).

The present invention particularly preferably provides that the rotor of the rotor-stator system is a propeller stirrer having at least 2 rotor blades, in particular 3, in particular 4, in particular 5 rotor blades, preferably 3 rotor blades, each of which is at an angle of 36 to 180°, in particular 45 to 120°, in particular 72 to 90°, preferably 72° (calculated from the centre of one rotor blade tip to the next) to the adjacent rotor blade, which are inclined about the longitudinal axis of the rotor blade by 0°, in particular 1°, in particular 5°, in particular 10°, in particular 20°, in particular 30°, in particular 40°, in particular 45° (starting from rotor blades lying in a plane) and which have a specific shape, in particular a rectangular shape, a trapezoidal shape, double trapezoidal shape or rectangular trapezoidal shape.

In a preferred embodiment, the method according to the invention leads to crystal nuclei of 1,1-GPM dihydrate being formed in the nucleator, in particular being formed selectively, i.e. with at least partial, in particular complete exclusion of 1,6-GPS.

In a particularly preferred embodiment of the present invention, the method according to the invention makes it possible to provide a first isomalt-containing suspension in method step b), in which predominantly, in particular solely, crystal nuclei consisting of 1,1-GPM, in particular 1,1-GPM dihydrate, are present. In a preferred embodiment, the method according to the invention therefore provides, in particular in method step b), a particularly homogeneously composed first isomalt-containing suspension which, in a preferred embodiment, is characterised that all the crystal nuclei contained therein consist of 1,1-GPM, in particular 1,1-GPM dihydrate. Such an isomalt-containing suspension, containing predominantly 1,1-GPM seed crystals, in particular a first crystalline phase containing only 1,1-GPM seed crystals, is particularly suitable for the crystallisation following in method step c).

In an advantageous and particularly preferred manner, the method according to the invention results in increased work safety, since no dispersing medium, in particular alcohols, in particular isopropanol, is used in the flash evaporation, in particular through specific control of the shearing and/or process parameters compared to conventional crystal nucleation reactors, in particular slurry reactors, from which, in addition to increased work safety through reduced explosion risk, a reduction in operating costs also results. Furthermore, advantageously, no slurry has to be provided and supplemented in an upstream work step.

In an advantageous manner, the method according to the invention, in particular and in a preferred embodiment, can generate homogeneous crystal nuclei comprising 1,1-GPM, in particular consisting thereof, under control of the shear and/or the process parameters, in particular supersaturation, temperature and pressure, wherein the first liquid phase of the first isomalt-containing suspension comprises, in addition to solvent, dissolved 1,6-GPS, whereby particularly pure crystals comprising, in particular consisting of, 1,1-GPM or 1,6-GPS or 1,1-GPM and 1,6-GPS are obtained in the subsequent crystallisation process. This is based, without being bound to theory, on the very good growth properties of the crystal nuclei obtained in method step b) according to the invention, whereas in common technical reactors, in particular slurry reactors, process steps can lead to the formation of fracture edges, wherein in the case of continuous crystal growth these fracture edges represent a preferred site of crystal growth, i.e. crystallisation preferably takes place at these fracture edges. Preferred crystal growth at these fracture edges results in the inclusion of solvents, in particular water, or of the liquid phase present according to the invention, in particular the isomalt-containing liquid phase, in the crystal structure of the crystals obtained, whereby after obtaining the crystalline phase the crystals have impurities, in particular undesired inclusions.

In an advantageous manner, the method according to the invention obtains a particularly uniform crystal size distribution, in particular a crystal size distribution adjustable by controlling the shear and/or the process parameters, in the 1,1-GPM- and/or 1,6-GPS-enriched phases, so that they can be efficiently separated from other phases, in particular liquid phases.

The invention thus provides a particularly simple and efficient method for producing 1,1-GPM- and/or 1,6-GPS-enriched isomalt compositions from an isomalt-containing solution, in particular pure 1,1-GPM and/or pure 1,6-GPS, which makes use of different solubility products of 1,1-GPM and 1,6-GPS and wherein two separate phases are obtained, each having an increased, i.e. enriched, 1,1-GPM- or 1,6-GPS-content, respectively, compared to the 1,1-GPM-content or 1,6-GPS-content, respectively, of the isomalt-containing solution according to method step a). In particular, the method according to the invention makes it possible to obtain both a 1,1-GPM and a 1,6-GPS-enriched isomalt composition in a single method. According to the invention, it may also be provided to carry out the method according to the invention to obtain only a 1,1-GPM-enriched isomalt composition. According to a preferred embodiment of the invention, it may also be provided to carry out the method according to the invention to provide only a 1,6-GPS-enriched isomalt composition.

In particular, the invention provides that in method step a) an isomalt-containing solution is provided which has a content of 65 to 90 wt. % isomalt (based on the total weight of the isomalt-containing solution).

In a preferred embodiment according to the invention, the isomalt-containing solution provided in method step a) has 70 to 85 wt. %, in particular 70 to 80 wt. % isomalt, preferably 72 to 80 wt. %, preferably 74 to 80 wt. %, preferably 76 to 80 wt. %, preferably 70 to 78 wt. %, preferably 74 to 76 wt. %, preferably 70 to 74 wt. %, preferably 70 to 75 wt. %, preferably 70 to 76 wt. %, preferably 72 to 76 wt. %, preferably 74 to 76 wt. %, preferably 75 to 80 wt. %, or preferably 76 to 80 wt. % (each based on the total weight of the isomalt-containing solution).

In a preferred embodiment according to the invention, the isomalt-containing solution provided in method step a) is a saturated solution, particularly preferably a supersaturated solution.

In a preferred embodiment according to the invention, the isomalt-containing solution provided in method step a) has a content of 1,1-GPM of 35 to 61 wt. %, preferably 46 to 56 wt. %, preferably 48 to 55 wt. %, preferably 49 to 54 wt. %, preferably 50 to 53 wt. % (each based on the total weight of the dry matter of the isomalt-containing solution).

In a preferred embodiment according to the invention, the isomalt-containing solution provided in method step a) has a content of 1,6-GPS of 39 to 65 wt. %, preferably 44 to 54 wt. %, preferably 45 to 52 wt. %, preferably 46 to 51 wt. %, preferably 47 to 50 wt. % (each based on the total weight of the dry matter of the isomalt-containing solution).

In a preferred embodiment according to the invention, the isomalt-containing solution provided in method step a) has a content of 1,1-GPM of 35 to 61 wt. %, preferably 46 to 56 wt. %, preferably 48 to 55 wt. %, preferably 49 to 54 wt. %, preferably 50 to 53 wt. % 1,1-GPM and a content of 1,6-GPS of 39 to 65 wt. %, preferably 44 to 54 wt. %, preferably 45 to 52 wt. %, preferably 46 to 51 wt. %, preferably 47 to 50 wt. % 1,6-GPS (each based on the total weight of the dry matter of the isomalt-containing solution).

In a preferred embodiment according to the invention, the isomalt-containing solution provided in method step a) has a content of 1,1-GPM of 35 to 44 wt. % and a content of 1,6-GPS of 56 to 65 wt. % (each based on the total weight of the dry matter of the isomalt-containing solution).

In a preferred embodiment according to the invention, the isomalt-containing solution provided in method step a) has a content of 1,1-GPM of 35 to 50 wt. %, preferably 37 to 48 wt. %, preferably 39 to 46 wt. %, preferably 39 to 44 wt. %, preferably 39 to 42 wt. % (each based on the total weight of the dry matter of the isomalt-containing solution).

In a preferred embodiment according to the invention, the isomalt-containing solution provided in method step a) has a content of 1,6-GPS of 50 to 65 wt. %, preferably 52 to 63 wt. %, preferably 54 to 61 wt. %, preferably 56 to 59 wt. %, preferably 58 to 59 wt. % (each based on the total weight of the dry matter of the isomalt-containing solution).

In a preferred embodiment according to the invention, the isomalt-containing solution provided in method step a) has a content of 1,1-GPM of 35 to 50 wt. %, preferably 37 to 48 wt. %, preferably 39 to 46 wt. %, preferably 41 to 44 wt. %, preferably 41 to 42 wt. % 1,1-GPM and a content of 1,6-GPS of 50 to 65 wt. %, preferably 52 to 63 wt. %, preferably 54 to 61 wt. %, preferably 56 to 59 wt. %, preferably 58 to 59 wt. % 1,6-GPS (each based on the total weight of the dry matter of the isomalt-containing solution).

In a preferred embodiment according to the invention, the isomalt-containing solution provided in method step a) has a content of 1,1-GPM of 35 to 50 wt. % and a content of 1,6-GPS of 50 to 65 wt. % (each based on the total weight of the dry matter of the isomalt-containing solution).

In a preferred embodiment according to the invention, the isomalt-containing solution provided in method step a) has a content of 1,1-GPM of 45 to 57 wt. %, preferably 47 to 56 wt. %, preferably 48 to 55 wt. %, preferably 49 to 54 wt. %, preferably 50 to 53 wt. % (based on the total weight of the dry matter of the isomalt-containing solution).

In a preferred embodiment according to the invention, the isomalt-containing solution provided in method step a) has a content of 1,6-GPS of 43 to 55 wt. %, preferably 44 to 53 wt. %, preferably 45 to 52 wt. %, preferably 46 to 51 wt. %, preferably 47 to 50 wt. % (based on the total weight of the dry matter of the isomalt-containing solution).

In a preferred embodiment according to the invention, the isomalt-containing solution provided in method step a) has a content of 1,1-GPM of 45 to 57 wt. %, preferably 47 to 56 wt. %, preferably 48 to 55 wt. %, preferably 49 to 54 wt. %, preferably 50 to 53 wt. % 1,1-GPM and a content of 1,6-GPS of 43 to 55 wt. %, preferably 44 to 53 wt. %, preferably 45 to 52 wt. %, preferably 46 to 51 wt. %, preferably 47 to 50 wt. % 1,6-GPS (each based on the total weight of the dry matter of the isomalt-containing solution).

In a preferred embodiment according to the invention, the isomalt-containing solution provided in method step a) has a content of 1,1-GPM of 45 to 57 wt. % and a content of 1,6-GPS of 43 to 55 wt. % (each based on the total weight of the dry matter of the isomalt-containing solution).

In a preferred embodiment according to the invention, the isomalt-containing solution provided in method step a) has a temperature of 50 to 90° C., preferably 60 to 90° C., preferably 61 to 85° C., preferably 64 to 85° C., preferably 50 to 80° C., preferably 60 to 80° C., preferably 60 to 75° C., preferably 64 to 75° C., or preferably 64 to 70° C. In a preferred embodiment, the isomalt-containing solution is adjusted to one of the aforementioned temperatures in method step a).

In a preferred embodiment according to the invention, the isomalt-containing solution provided in method step a) has 1,1-GPM, 1,6-GPS and at least one compound selected from the group consisting of 1,1-GPS, further deoxy-disaccharide alcohols, polysaccharides, oligosaccharides, trisaccharides, monosaccharides, disaccharides, sorbitol, mannitol and isomelezitose.

In a preferred embodiment according to the invention, the isomalt-containing solution provided in method step a) has 1,1-GPM, 1,6-GPS and at least one compound selected from the group consisting of 1,1-GPS, further deoxy-disaccharide alcohols, oligosaccharides, trisaccharides, monosaccharides, disaccharides, sorbitol, mannitol and isomelezitose.

In a preferred embodiment according to the invention, the isomalt-containing solution provided in method step a) and further processed in method steps b) and c) has no compounds other than water, 1,1-GPM, 1,6-GPS and the at least one compound selected from the group consisting of 1,1-GPS, further deoxy-disaccharide alcohols, oligosaccharides, trisaccharides, monosaccharides, disaccharides, sorbitol, mannitol and isomelezitose.)

In a preferred embodiment according to the invention, the isomalt-containing solution provided in method step a) and further processed in method steps b) and c) has no gum arabic.

In a preferred embodiment according to the invention, the isomalt-containing solution provided in method step a) and further processed in method steps b) and c) does not have any compounds other than water and 1,1-GPM and 1,6-GPS.

In a preferred embodiment according to the invention, the isomalt-containing solution provided in method step a) is a solution of isomalt in a solvent, in particular water, ethanol, propanol, isopropanol, butanol, isobutanol or mixtures thereof. In a particularly preferred embodiment, the isomalt-containing solution provided in method step a) is an aqueous solution containing small amounts of ethanol, propanol, isopropanol, butanol and/or isobutanol, in particular 0.1 to 5 vol. % of the alcohols based on the total aqueous solution. In a further particularly preferred embodiment, the solvent of the isomalt-containing solution provided in method step a) is water, in particular fully demineralised water. Preferably, the isomalt-containing solution provided in method step a) does not comprise any organic solvents.

In a preferred embodiment according to the invention, the isomalt-containing solution provided in method step a) is an aqueous solution, in particular an aqueous solution which has a pH range of 3.0 to 8.0, preferably 3.5 to 7, 5, preferably 4.0 to 7.0, preferably 4.3 to 6.5, preferably 4.6 to 6.0, preferably 4.8 to 5.5, or preferably 4.9 to 5.5, preferably having a pH of 4.9, preferably 6.0, preferably 8.0, preferably 4.5, preferably 4.0, preferably 3.5, preferably 3.0.

In a preferred embodiment according to the invention, an isomalt-containing solution is produced directly from isomalt and water, optionally from isomalt, water and further previously listed components.

In a preferred embodiment according to the invention, the isomalt-containing solution provided in method step a) is obtained in a method step a1) taking place before method step a) from an isomalt-containing initial solution or suspension by evaporation or reverse osmosis. In a preferred embodiment according to the invention, in method step a1) the isomalt-containing solution provided according to the invention in method step a) is obtained from an initial solution or suspension of isomalt in water by increasing the temperature of the solution or suspension, in particular at a pressure reduced relative to atmospheric pressure.

In a preferred embodiment according to the invention, in method step a1) the isomalt-containing solution provided according to the invention in method step a) is produced from an initial solution or suspension of isomalt in water by reverse osmosis, in particular at a pressure increased relative to atmospheric pressure.

In a preferred embodiment according to the invention, in method step a1) the isomalt-containing solution provided according to the invention in method step a) is produced by adding crystalline isomalt to water, in particular demineralised water. In a preferred embodiment according to the invention, in method step a1) the isomalt-containing solution provided according to the invention in method step a) is produced by adding crystalline isomalt to a lower-concentration initial solution or suspension which has isomalt.

In a preferred embodiment according to the invention, in step a1) the isomalt-containing solution provided in step a) is produced from an initial solution or suspension which has isomalt by concentrating the initial solution, preferably by evaporation, in particular at a pressure reduced relative to atmospheric pressure, reverse osmosis, in particular at a pressure increased relative to atmospheric pressure, and/or addition of crystalline isomalt, or by diluting the initial solution or suspension, preferably by addition of water, and thus obtaining the isomalt-containing solution provided in step a).

In a preferred embodiment according to the invention, the isomalt-containing initial solution or suspension used for method step a1) is obtained by selective hydrogenation, in particular 1,6-GPS-selective hydrogenation.

In a preferred embodiment according to the invention, the isomalt-containing initial solution used for method step a1) is obtained by selective hydrogenation, in particular by selective hydrogenation by means of a hydrogenation catalyst, in particular a hydrogenation catalyst comprising, in particular consisting of, ruthenium or ruthenium oxide and a catalyst support.

In a preferred embodiment according to the invention, the isomalt-containing initial solution used for method step a1) is obtained by selective hydrogenation, in particular by selective hydrogenation by means of a hydrogenation catalyst comprising, in particular consisting of, nickel, Raney-nickel or supported nickel.

In a preferred embodiment according to the invention, the isomalt-containing initial solution obtained in method step a1) has a temperature of 50 to 95° C., in particular 55 to 90° C., in particular 60 to 85° ° C., in particular 65 to 80° C., preferably 65 to 70° C.

In a particularly preferred embodiment, the isomalt-containing initial solution obtained in method step a1) has a temperature at least 10° C. higher, preferably at least 8° C., preferably at least 5° C., or preferably at least 3° C., in comparison to the isomalt-containing solution provided in method step a). Preferably, the isomalt-containing solution obtained in method step a1) is cooled to a temperature to be preferably used in method step a).

In a preferred embodiment according to the invention, method step a1) takes place in an evaporator.

After method step a) and before method step c), the method according to the invention comprises a nucleation by means of flash evaporation in a method step b).

In a preferred embodiment according to the invention, the temperature of the isomalt-containing solution is adjusted after method step a) and before method step b). Preferably according to the invention, the temperature of the isomalt-containing solution supplied is adjusted to 50 to 90° C., preferably to 55 to 80° C., particularly preferably to 60 to 75° C., before flash evaporation, i.e. after method step a) and before method step b).

Preferably, the isomalt-containing solution provided in method step a) has a temperature of 50 to 90° C., preferably 55 to 80° C., particularly preferably 60 to 75° C.

In a preferred embodiment according to the invention, the flash evaporation according to method step b) is carried out continuously.

In a preferred embodiment according to the invention, the flash evaporation according to method step b) is carried out discontinuously.

In a preferred embodiment according to the invention, during the flash evaporation according to method step b), after method step a) and before method step c), the absolute pressure is reduced by at least 5%, preferably by at least 10%, preferably by at least 50%, preferably by at least 70%, or preferably by at least 90% (each based on the originally prevailing absolute atmospheric pressure).

Method steps a1), a), c), d) and e) preferably take place at an increased pressure compared to method step b).

Method steps a), c), d) and e) preferably take place at an increased pressure compared to method step b).

Method steps a1), a), d) and e) preferably take place at an increased pressure compared to method step b).

Method steps a), d) and e) preferably take place at an increased pressure compared to method step b).

Method steps a1), a), c), d) and e) preferably take place at atmospheric pressure.

Method steps a), c), d) and e) preferably take place at atmospheric pressure.

Method steps a1), a), d) and e) preferably take place at atmospheric pressure.

Method steps a), d) and e) preferably take place at atmospheric pressure.

In a particularly preferred embodiment, method step c) is carried out under atmospheric pressure if method step c) is carried out in the form of a cooling crystallisation or an isothermal crystallisation. If method step c) is carried out as an evaporation crystallisation, method step c) preferably takes place at a reduced pressure compared to atmospheric pressure, in particular vacuum.

In a particularly preferred embodiment according to the invention, during flash evaporation according to method step b) after method step a) and before method step c), the absolute pressure is reduced, preferably to 10 to 500 mbar, preferably to 20 to 400 mbar, preferably 30 to 300 mbar, preferably 50 to 200 mbar, preferably 90 to 110 mbar, in particular 90 to 100 mbar.

In a further preferred embodiment of the present invention, during flash evaporation according to method step b) after method step a) and before method step c), the absolute pressure is reduced to at most 500 mbar, preferably at most 400 mbar, preferably at most 300 mbar, preferably at most 200 mbar, preferably at most 150 mbar, preferably at most 100 mbar, preferably at most 80 mbar, preferably at most 50 mbar, preferably at most 20 mbar, preferably at most 10 mbar.

In a further preferred embodiment according to the invention, the flash evaporation according to method step b) is carried out after method step a) and before method step c) at a temperature in the range from 30 to 70° C., preferably 35 to 65° C., preferably 30 to 60° ° C., preferably 40 to 60° C., preferably 45 to 55° C., preferably 50 to 55° C.

In a further preferred embodiment according to the invention, the flash evaporation according to method step b) is carried out after method step a) and before method step c) at a temperature in the range from 30 to 70° C., preferably 35 to 65° ° C., preferably 40 to 60° C., preferably 30 to 60° C., preferably 45 to 55° C., preferably 50 to 55° C. and at reduced absolute pressure, preferably at 10 to 500 mbar, preferably at 20 to 400 mbar, preferably 30 to 300 mbar, preferably 50 to 200 mbar, preferably 90 to 110 mbar, in particular at 90 to 100 mbar and 50 to 55° C.

In a preferred embodiment according to the invention, during the flash evaporation according to method step b) after method step a) and before method step c), the isomalt-containing solution provided in method step a) is subjected to reduced absolute pressure that 10 to 50%, in particular 15 to 40%, in particular 20 to 30% of the amount of dissolved 1,1-GPM contained in the isomalt-containing solution provided by method step a) has passed into the first crystalline phase and thus an enrichment of 1,1-GPM in the first crystalline phase and an enrichment of 1,6-GPS in the first liquid phase is achieved.

Method step b) can preferably be carried out for a period of 2 minutes to 12 hours, 3 minutes to 10 hours, preferably 4 minutes to 9 hours, preferably 1 to 12 hours, preferably 2 to 8 hours, preferably 3 to 7 hours, preferably 4 to 6 hours, preferably 1 to 5 hours, preferably 2 to 5 hours, preferably 3 to 5 hours, preferably 4 to 5 hours, preferably for 5 hours.

In a preferred embodiment according to the invention, method step b) is carried out such that during method step b) 20 to 30% of the dissolved 1,1-GPM present in method step a) passes into the first crystalline phase (based on the total weight of the dry matter (DM) of 1,1-GPM in the solution provided in method step a)).

In a preferred embodiment according to the invention, the flash evaporation according to method step b) is carried out after method step a) and before method step c) such that during method step b) the dry matter content of the isomalt-containing solution provided in method step a) is increased by 1 to 10 wt. %, preferably 1 to 8 wt. %, preferably 1 to 6 wt. % (based on the total weight of the dry matter (DM) of the isomalt-containing solution provided and the first isomalt-containing suspension obtained).

In a preferred embodiment according to the invention, in the first crystalline phase of the first isomalt-containing suspension obtained after the flash evaporation according to method step b) a content of 1,1-GPM of 57 to 100 wt. %, preferably 60 to 100 wt. %, preferably 62 to 99 wt. %, preferably 65 to 99 wt. %, preferably 67 to 95 wt. % 1,1-GPM as well as a content of 1,6-GPS of 0 to 43 wt. %, preferably 0 to 40 wt. %, preferably 1 to 38 wt. %, preferably 1 to 35 wt. %, preferably 5 to 33 wt. % 1,6-GPS (each based on the total weight of the dry matter of the first crystalline phase of the suspension obtained according to method step b)) is present.

In a preferred embodiment according to the invention, in the first liquid phase of the first isomalt-containing suspension obtained after flash evaporation according to method step b) a content of 1,1-GPM of 25 to 35 wt. %, preferably 28 to 34 wt. %, preferably 29 to 33 wt. %, preferably 30 to 32 wt. %, preferably 31 wt. % 1,1-GPM, as well as a content of 1,6-GPS of 65 to 75 wt. %, preferably 66 to 72 wt. %, preferably 67 to 71 wt. %, preferably 68 to 70 wt. %, preferably 68 wt. % 1,6-GPS (each based on the total weight of the dry matter remaining in the first liquid phase after method step b)) is present.

In a preferred embodiment according to the invention, in the first liquid phase of the first isomalt-containing suspension obtained after the flash evaporation according to method step b) a dry matter content of 56 to 80 wt. %, preferably 69 to 74 wt. %, preferably 70 to 73 wt. %, preferably 71 to 72 wt. % (based on the total weight of the first suspension present after method step b)) is present.

In a preferred embodiment according to the invention, no inoculation with seed crystals, in particular isomalt, 1,1-GPM and/or 1,6-GPS, takes place during method step b).

In a preferred embodiment according to the invention, the crystallisation process according to method step c) is carried out in a crystalliser.

In method step c), the first isomalt-containing suspension is preferably subjected to conditions which do not allow complete solubility of isomalt in the first liquid phase used, so that further crystallisation of isomalt, preferably 1,1-GPM, takes place, in particular the first crystalline phase is further enriched with 1,1-GPM and the first liquid phase is further enriched with 1,6-GPS to obtain a second suspension comprising a second crystalline phase and a second liquid phase, wherein the second crystalline phase is preferably 1,1-GPM-enriched and the second liquid phase is preferably 1,6-GPS-enriched. In a preferred embodiment, 1,6-GPS and 1,1-GPM are thereby present partially dissolved and partially undissolved.

In a preferred embodiment according to the invention, crystallisation according to method step c) can be carried out continuously.

In a preferred embodiment according to the invention, the crystallisation according to method step c) can be carried out discontinuously.

In a preferred embodiment according to the invention, the crystallisation in method step c) is an isothermal crystallisation, a cooling crystallisation and/or an evaporation crystallisation, in particular a multi-stage evaporation crystallisation.

In a preferred embodiment according to the invention, the first isomalt-containing suspension obtained from method step b) is subjected to crystallisation, preferably isothermal crystallisation, in method step c). According to the invention, preferably when isothermal crystallisation is used, the temperature of the first isomalt-containing suspension is adjusted to 50 to 60° C., preferably 52 to 60° C., preferably 54 to 60° C., preferably 51 to 59° C., preferably 52 to 59° C., preferably 53 to 59° ° C., preferably 54 to 59° C., preferably 52 to 58° C., preferably 53 to 57° C., preferably 53 to 58° C., preferably 54 to 58° C., preferably 54 to 57° C., or preferably 54 to 56° C.

In a preferred embodiment according to the invention, the temperature of the isothermal crystallisation in method step c) is 50 to 60° C., preferably 51 to 60° C., preferably 52 to 60° C., preferably 53 to 59° C., preferably 50 to 59° C., preferably 51 to 59° C., preferably 52 to 58° C., preferably 53 to 58° C., preferably 54 to 60° C., preferably 54 to 58° C., preferably 54 to 56° C., preferably 53 to 57° C., preferably 53 to 56° C., or preferably 54 to 56° C. In a particularly preferred embodiment according to the invention, the isothermal crystallisation carried out in step c) takes place at the temperature set in step c), wherein released crystallisation energy is continuously dissipated.

In a preferred embodiment according to the invention, the isothermal crystallisation of the isomalt-containing suspension in method step c) is carried out over a period of 10 to 100 hours, preferably 20 to 100 hours, preferably 20 to 80 hours, preferably 20 to 60 hours, preferably 20 to 52 hours, preferably 20 to 40 hours, preferably 30 to 80 hours, preferably 30 to 70 hours, preferably 30 to 60 hours, preferably 30 to 50 hours or preferably 30 to 40 hours.

In an advantageous manner, carrying out method step c) by means of isothermal crystallisation results in a homogeneous crystal size distribution, since, without being bound by theory, the steady decrease in supersaturation as crystallisation progresses minimises the risk of fine grain formation at later times in the process. Furthermore, this mode of operation leads to an extension of the service life of the reactor used for crystallisation because a reduced formation of deposits and/or reduced incrustations can be observed compared to other crystallisations, in particular cooling crystallisations with the use of a cooling ramp. Without being bound by theory, the reduced formation of deposits and/or incrustations are based on only small temperature differences between the cooling elements used and the isomalt-containing suspension (magma) used.

In a preferred embodiment according to the invention, the first isomalt-containing suspension obtained from method step b) is subjected to crystallisation, preferably cooling crystallisation, in method step c). According to the invention, when a cooling crystallisation is used, the temperature of the cooling crystallisation in method step c) is reduced stepwise preferably by at most 2 K/h, preferably at most 1 K/h, preferably at most 0.8 K/h, preferably at most 0.6 K/h, preferably at most 0.4 K/h, preferably at most 0.2 K/h, particularly preferably at most 0.1 K/h, in order to additionally increase the yield of 1,1-GPM-enriched crystals. Preferred is a cooling rate of 0.8 to 1.5 K/h, preferably starting at a temperature of 65° C. and ending at 37° C.

In a preferred embodiment according to the invention, the cooling crystallisation of the isomalt-containing suspension in method step c) is carried out over a period of 10 to 100 hours, preferably 20 to 100 hours, preferably 20 to 80 hours, preferably 20 to 60 hours, preferably 20 to 52 hours, preferably 20 to 40 hours, preferably 30 to 80 hours, preferably 30 to 70 hours, preferably 30 to 60 hours, preferably 30 to 50 hours or preferably 30 to 40 hours.

In a preferred embodiment according to the invention, crystallisation, in particular evaporation crystallisation, in particular multi-stage evaporation crystallisation, is affected by increasing the concentration of the first isomalt-containing suspension obtained from method step b) in method step c), in particular the concentration of the isomalt in the liquid phase of the first isomalt-containing suspension is increased, in particular by a multiple-effect evaporator.

In a preferred embodiment according to the invention, the multiple-effect evaporator has at least two reactors, preferably at least 3 reactors, preferably at least 4 reactors, preferably at least 5 reactors, preferably at least 6 reactors, preferably at least 7, preferably at most 3 reactors, preferably at most 4 reactors, preferably at most 5 reactors, preferably at most 6 reactors, preferably at most 7 reactors.

In a preferred embodiment according to the invention, the multiple-effect evaporator removes all or part of at least one solvent, preferably one solvent, preferably several solvents, in particular preferably water and at least one alcohol. Preferably according to the invention, the concentration of the isomalt in the liquid phase of the second isomalt-containing suspension in method step c) is preferably adjusted such that the amount of solvent is not sufficient to dissolve the entire amount of isomalt at a predetermined temperature.

In a preferred embodiment according to the invention, the pressure in the multiple-effect evaporator in method step c) is 0.01 to 2 bar, preferably 0.01 to 1 bar, preferably 0.01 to 0.5 bar, preferably 0.1 to 1 bar, preferably 0.1 to 0.5 bar.

In a preferred embodiment according to the invention, the evaporation crystallisation in method step c) in the respective reactors of the multiple-effect evaporator is in each case, i.e., per reactor, an isothermal crystallisation.

In a preferred embodiment according to the invention, the pressure in a following reactor in the multiple-effect evaporator in method step c) is reduced by at least 5% compared to a preceding reactor, preferably by at least 10%, preferably by at least 12%, preferably by at least 15%, or preferably by at least 20%.

In a preferred embodiment according to the invention, the temperature in a following reactor in the multiple effect evaporator in method step c) is reduced by at least 5% compared to a preceding reactor, preferably by at least 10%, preferably by at least 12%, preferably by at least 15%, or preferably by at least 20%.

The quantitative ratio of 1,1-GPM and 1,6-GPS in the 1,1-GPM-enriched second crystalline phase and in the 1,6-GPS-enriched second liquid phase can be adjusted by the temperature and/or the pressure, in particular the temperature profile and/or the pressure profile in the individual reactors in the multiple-effect evaporator.

In a preferred embodiment according to the invention, the evaporation crystallisation of the isomalt-containing suspension in method step c) is carried out over a period of 1 minute to 14 hours, in particular by a multiple-effect evaporator.

In a preferred embodiment according to the invention, no inoculation with seed crystals, in particular isomalt, 1,1-GPM and/or 1,6-GPS, takes place during the crystallisation in method step c).

In a preferred embodiment according to the invention, no inoculation with seed crystals, in particular isomalt, 1,1-GPM and/or 1,6-GPS, takes place during the method, in particular during an isothermal crystallisation in method step c) preferred according to the invention.

In a preferred embodiment according to the invention, no inoculation with seed crystals, in particular isomalt, 1,1-GPM and/or 1,6-GPS, takes place during method steps b) and c).

In a further preferred embodiment according to the invention, crystalline isomalt, 1,1-GPM or 1,6-GPS is added in pure or almost pure form as seed crystal in method step c). After introduction of seed crystals into the isomalt-containing solution, the more easily soluble 1,6-GPS crystals dissolve, while the less soluble 1,1-GPM crystals remain as crystallisation nuclei.

In a preferred embodiment according to the invention, the 1,1-GPM-enriched second crystalline phase in method step c) has a mixture of 1,1-GPM and 1,6-GPS with 57 to 99 wt. % 1,1-GPM and 43 to 1 wt. % 1,6-GPS, preferably from 60 to 80 wt. % 1,1-GPM and 20 to 40 wt. % 1,6-GPS, preferably 60 to 75 wt. % 1,1-GPM and 25 to 40 wt. % 1,6-GPS, preferably 65 to 75 wt. % 1,1-GPM and 25 to 35 wt. % 1,6-GPS (each based on the total weight of the dry matter (DM) of the second crystalline phase).

In a preferred embodiment according to the invention, the 1,6-GPS-enriched second liquid phase in method step c) has a mixture of 1,1-GPM and 1,6-GPS with 43 to 1 wt. % 1,1-GPM and 57 to 99 wt. % 1,6-GPS, preferably 20 to 25 wt. % 1,1-GPM and 80 to 75 wt. % 1,6-GPS (each based on the total weight of the dry matter (DM) of the second liquid phase).

In a preferred embodiment according to the invention, the second crystalline phase separated in method step d) has at least 60 wt. % 1,1-GPM, preferably at least 67 wt. %, preferably at least 75 wt. %, preferably at least 80 wt. %, preferably at least 85 wt. %, preferably at least 90 wt. %, or preferably at least 95 wt. % (each based on the total weight (DM) of the second crystalline phase).

In a particularly preferred embodiment, the second crystalline phase separated in method step d) has at least 99 wt. %, in particular 100 wt. % 1,1-GPM (based on the total weight (DM) of the second crystalline phase).

In a preferred embodiment according to the invention, the second crystalline phase separated in method step d) has at most 40 wt. % 1,6-GPM, preferably at most 32 wt. %, preferably at most 25 wt. %, preferably at most 20 wt. %, preferably at most 15 wt. %, preferably at most 10 wt. %, or preferably at most 5 wt. % (each based on the total weight (DM) of the second crystalline phase).

In a particularly preferred embodiment, the second crystalline phase separated in method step d) has at most 1 wt. %, in particular 0 wt. %, of 1,6-GPS (based on the total weight (DM) of the second crystalline phase).

In a particularly preferred embodiment according to the invention, the crystalline phase separated in method step d) has no or almost no 1,6-GPS.

In a preferred embodiment according to the invention, the second crystalline phase separated in method step d) has 60 to 75 wt. % 1,1-GPM, in particular 60 to 72 wt. % 1,1-GPM, preferably 65 to 71 wt. %, preferably 66 to 70 wt. %, 67 to 69 wt. %, preferably 68 wt. % (each based on the total weight of the second crystalline phase) of 1,1-GPM and 25 to 40 wt. %, in particular 28 to 40 wt. % of 1,6-GPS, preferably 29 to 35 wt. %, preferably 30 to 34 wt. %, 31 to 33 wt. %, preferably 32 wt. % of 1,6-GPS (each based on the total weight (DM) of the second crystalline phase).

In a preferred embodiment according to the invention, the second crystalline phase separated in method step d) has 60 to 75 wt. % 1,1-GPM, in particular 65 to 71 wt. %, 1,1-GPM (each based on the total weight of the second crystalline phase) and 25 to 40 wt. %, in particular 29 to 35 wt. %, 1,6-GPS (each based on the total weight (DM) of the second crystalline phase).

In a preferred embodiment according to the invention, the second crystalline phase separated in method step d) has a length-to-width ratio of the crystals contained therein of from 7.0 to 10.5, in particular from 7.5 to 10.0, in particular from 7.5 to 9.0, in particular from 7.5 to 8.5, in particular from 8.0 (each mean value).

In a preferred embodiment according to the invention, the second crystalline phase separated in method step d) has a length-to-width ratio of the crystals contained therein of from 6.5 to 10.0, in particular from 7.0 to 9.5, in particular from 7.5 to 9.0, in particular from 7.5 to 8.5, in particular from 7.8 (each median).

In a preferred embodiment according to the invention, the second liquid phase separated in method step d) has 15 to 32 wt. % 1,1-GPM, preferably 17 to 30 wt. %, preferably 19 to 28 wt. %, 20 to 26 wt. %, preferably 21 to 24 wt. % (each based on the total weight of the dry matter (DM) of the second liquid phase).

In a preferred embodiment according to the invention, the second liquid phase separated in method step d) has at least 72 wt. % 1,6-GPS, preferably at least 75 wt. %, preferably at least 80 wt. %, preferably at least 85 wt. %, or preferably at least 90 wt. % (each based on the total weight of the dry matter (DM) of the second liquid phase).

In a preferred embodiment according to the invention, the second liquid phase separated in method step d) has 68 to 85 wt. % 1,6-GPS, preferably 70 to 83 wt. %, preferably 72 to 81 wt. %, 74 to 80 wt. %, preferably 76 to 79 wt. % (each based on the total weight of the dry matter (DM) of the second liquid phase).

In a preferred embodiment according to the invention, the second liquid phase separated in method step d) has 15 to 32 wt. % 1,1-GPM, preferably 17 to 30 wt. %, preferably 19 to 28 wt. %, preferably 20 to 26 wt. %, preferably 21 to 24 wt. % (each based on the total weight of the dry matter (DM) of the second liquid phase) of 1,1-GPM and 68 to 85 wt. % of 1,6-GPS, preferably 70 to 83 wt. %, preferably 72 to 81 wt. %, preferably 74 to 80 wt. %, preferably 76 to 79 wt. % of 1,6-GPS (each based on the total weight of the dry matter (DM) of the second liquid phase).

In a preferred embodiment according to the invention, the second liquid phase separated in method step d) has 15 to 32 wt. % 1,1-GPM (based on the total weight of the dry matter (DM) of the second liquid phase) and 68 to 85 wt. % 1,6-GPS (based on the total weight of the dry matter (DM) of the second liquid phase).

In a preferred embodiment according to the invention, the 1,1-GPM-enriched separated second crystalline phase contains at most 20 wt. % water, preferably at most 18 wt. % water, preferably at most 15 wt. % water, preferably at most 13 wt. % water, preferably 5 to 20 wt. % water, preferably 8 to 18 wt. % water, preferably 10 to 15 wt. % water, or preferably 11 to 13 wt. % water (each based on the total weight of the 1,1-GPM-enriched second crystalline phase).

In a preferred embodiment according to the invention, the 1,1-GPM-enriched second crystalline phase is separated from the 1,6-GPS-enriched second liquid phase in method step d) by decantation, filtration, sedimentation or centrifugation, in particular preferably by centrifugation. A separation provided according to the invention, in particular centrifugation, results in a separation of the second liquid phase from the second crystalline phase enriched with 1,1-GPM, while the second liquid phase is enriched with 1,6-GPS.

The separated 1,1-GPM-enriched second crystalline phase can be further processed in further purification and concentration steps to a 1,1-GPM-enriched composition, in particular to crystalline 1,1-GPM with a purity of at least 95 wt. %, preferably at least 96 wt. %, preferably at least 97 wt. %, preferably at least 98 wt. % or preferably at least 99 wt. % (each weight of 1,1-GPM based on the total weight (DM) of the composition).

In a preferred embodiment according to the invention, after method step d) the 1,1-GPM-enriched second crystalline phase is dried and obtained as a solid 1,1-GPM-enriched isomalt composition in method step e).

In a preferred embodiment according to the invention, the 1,6-GPS-enriched second liquid phase is concentrated at least once after method step d), preferably concentrated at least twice or preferably concentrated at least three times, and in method step e) obtained as a liquid 1,6-GPS-enriched isomalt composition.

In a preferred embodiment according to the invention, the 1,6-GPS-enriched second liquid phase is concentrated after method step d) to at least 60 wt. % dry matter content, preferably at least 65 wt. %, preferably at least 70 wt. %, preferably at least 75 wt. %, preferably at least 80 wt. %, preferably at least 85 wt. %, preferably at least 90 wt. %, or preferably at least 95 wt. % (each based on the total weight of the composition) and obtained in method step e) as a liquid 1,6-GPS-enriched isomalt composition.

In a further preferred embodiment according to the invention, the 1,6-GPS-enriched second liquid phase is processed in further purification and concentration steps to give a 1,6-GPS-enriched isomalt composition, in particular crystalline 1,6-GPS with a dry matter content of at least 95 wt. %, preferably at least 96 wt. %, preferably at least 97 wt. %, preferably at least 98 wt. %, or preferably at least 99 wt. % (each based on the total weight of the dry matter (DM) of the isomalt composition).

In a preferred embodiment according to the invention, the 1,6-GPS-enriched isomalt composition is obtained from the 1,6-GPS-enriched second liquid phase by concentrating and subsequently cooling-crystallising the 1,6-GPS-enriched second liquid phase, preferably the cooling crystallisation takes place in a temperature range of 40 to 60° C., preferably 50 to 60° C., preferably 40 to 50° C., or preferably 45 to 55° C., and preferably at cooling rates of 0.1 to 0.3 K/h, preferably 0.2 to 0.3 K/h, or preferably 0.1 to 0.2 K/h. The concentration and the cooling crystallisation are optionally repeated under the same conditions until a desired amount of crystals is obtained.

In a preferred embodiment according to the invention, after method step d) the 1,6-GPS-enriched second liquid phase is dried and in method step e) a solid 1,6-GPS-enriched isomalt composition is obtained.

In a preferred embodiment according to the invention, the 1,6-GPS-enriched second liquid phase is dried after method step d) and obtained in method step e) as a solid 1,6-GPS-enriched isomalt composition, in particular as a crystalline phase product.

In a preferred embodiment according to the invention, the dried 1,6-GPS-enriched composition preferably contains 0.05 to 6 wt. % water, preferably 2.0 to 3.0 wt. % water, preferably 0.05 to 2.5 wt. % water, preferably 0.05 to 1 wt. % water, preferably 0.1 to 0.5 wt. % water, preferably 0.1 to 0.5 wt. % water. % water, preferably a maximum of 6.0 wt. % water, preferably a maximum of 4.0 wt. % water, preferably a maximum of 2.5 wt. % water, preferably a maximum of 2.0 wt. % water, preferably a maximum of 1.0 wt. % water or preferably a maximum of 0.5 wt. % water (each based on the total weight of the 1,6-GPS-enriched crystalline composition).

In a further aspect, the present invention provides 1,1-GPM- and/or 1,6-GPS-enriched isomalt compositions producible by the method according to the invention, in particular produced.

In a preferred embodiment according to the invention, the 1,1-GPM-enriched isomalt composition has 60 to 72 wt. % 1,1-GPM, preferably 65 to 71 wt. %, preferably 66 to 70 wt. %, preferably 67 to 69 wt. %, preferably 67 or 68 wt. % (each based on the total weight of the dry matter (DM) of the 1,1-GPM-enriched composition).

In a further preferred embodiment of the present invention, the 1,6-GPS-enriched isomalt composition of the present invention has 15 to 32 wt. % 1,1-GPM, preferably 17 to 30 wt. %, preferably 19 to 28 wt. %, preferably 20 to 26 wt. %, preferably 21 to 14 wt. % 1,1-GPM and 68 to 85 wt. %, in particular 70 to 83 wt. %, in particular 72 to 81 wt. %, in particular 74 to 80 wt. %, in particular 76 to 79 wt. % 1,6-GPS (each based on the total weight of the dry matter (DM) of the 1,6-GPS-enriched composition).

In a preferred embodiment, the invention relates to a 1,1-GPM-enriched isomalt composition having 60 to 75 wt. % 1,1-GPM and 25 to 40 wt. % 1,6-GPS, in particular producible by a method according to the invention (each based on the total weight of the dry matter (DM) of the composition).

In a preferred embodiment, the invention relates to a 1,1-GPM-enriched isomalt composition having 60 to 75 wt. % 1,1-GPM and 25 to 40 wt. % 1,6 GPS (each based on the total weight of the dry matter (DM) of the total amount of 1,1-GPM and 1,6-GPS), in particular producible by a method according to the invention, in particular with a 1,1-GPM-content of at least 60 wt. % (based on the total weight of the dry matter (DM) of the composition).

In a preferred embodiment, the invention relates to a 1,6-GPS-enriched isomalt composition having 15 to 32 wt. % 1,1-GPM and 68 to 85 wt. % 1,6 GPS, in particular producible by a method according to the invention (each based on the total weight of the dry matter (DM) of the composition).

In a preferred embodiment, the invention relates to a 1,6-GPS-enriched isomalt composition having 15 to 32 wt. % 1,1-GPM and 68 to 85 wt. % 1,6 GPS (each based on the total weight of the dry matter (DM) of the total amount of 1,1-GPM and 1,6-GPS), in particular producible by a method according to the invention, in particular with a 1,6-GPS-content of at least 68 wt. % (based on the total weight of the dry matter (DM) of the composition).

In a preferred embodiment according to the invention, the 1,1-GPM-enriched isomalt composition obtained in method step e) has at least 61 wt. % 1,1-GPM, preferably at least 75 wt. %, preferably at least 80 wt. %, preferably at least 85 wt. %, preferably at least 90 wt. %, preferably at least 94 wt. %, preferably at least 95 wt. %, preferably at least 96 wt. %, preferably at least 99 wt. %, preferably 75 to 95 wt. %, preferably 75 to 90 wt. %, preferably 75 to 85 wt. %, or preferably 80 to 99 wt. % (each based on the total weight of the dry matter (DM) of the 1,1-GPM-enriched isomalt composition).

In a preferred embodiment according to the invention, the 1,6-GPS-enriched isomalt composition obtained in method step e) has at least 72 wt. % 1,6-GPS, preferably at least 75 wt. %, preferably at least 80 wt. %, preferably at least 85 wt. %, preferably at least 90 wt. %, preferably at least 95 wt. %, preferably at least 99 wt. %, preferably 72 to 95 wt. %, preferably 72 to 90 wt. %, preferably 72 to 85 wt. %, or preferably 80 to 99 wt. % (each based on the total weight of the dry matter (DM) of the 1,6-GPS-enriched isomalt composition).

In a preferred embodiment according to the invention, the 1,1-GPM- and/or 1,6-GPS-enriched isomalt composition is present in crystalline form.

In a preferred embodiment according to the invention, the 1,1-GPM-enriched isomalt composition according to the invention, which preferably is one or more of the preferred 1,1-GPM-enriched isomalt compositions according to the invention characterised above, has a length-to-width ratio of the crystals contained therein of from 7.0 to 10.5, in particular from 7.5 to 10.0, in particular from 7.5 to 9.0, in particular from 7.5 to 8.5, in particular from 8.0 (each mean value).

In a preferred embodiment according to the invention, the 1,1-GPM-enriched isomalt composition according to the invention, which preferably is one or more of the preferred 1, 1,1-GPM-enriched isomalt compositions according to the invention characterised above, has a length-to-width ratio of the crystals contained therein of from 6.5 to 10.0, in particular from 7.0 to 9.5, in particular from 7.5 to 9.0, in particular from 7.5 to 8.5, in particular from 7.8 (each median).

In a further preferred embodiment, the 1,1-GPM- and/or 1,6-GPS-enriched isomalt composition is present in semicrystalline or amorphous form.

In a preferred embodiment according to the invention, the 1,1-GPM- and/or 1,6-GPS-enriched isomalt composition according to the invention has, in addition to the 1,1-GPM and 1,6-GPS components, at least one further component selected from the group consisting of mannitol, sorbitol, sucrose, 1,1-GPS (1-O-α-D-glucopyranosyl-D-sorbitol), glycosylglycitols, deoxy-disaccharide alcohols, GPI (glucopyranosyl-iditol), isomaltose, isomaltulose and isomelezitose.

In a preferred embodiment according to the invention, the 1,1-GPM- and/or 1,6-GPS-enriched isomalt composition according to the invention has 0.01 to 0.3 wt. % mannitol, preferably 0.01 to 0.2 wt. %, preferably 0.01 to 0.1 wt. %, preferably 0.01 to 0.06 wt. %, 0.02 to 0.3 wt. %, preferably 0.02 to 0.2 wt. %, preferably 0.02 to 0.1 wt. %, or preferably 0.02 to 0.06 wt. %, preferably at most 0.3 wt. % mannitol, preferably at most 0.2 wt. %, preferably at most 0.1 wt. %, or preferably at most 0.06 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain mannitol.

In a preferred embodiment according to the invention, the 1,1-GPM- and/or 1,6-GPS-enriched isomalt composition according to the invention has 0.01 to 0.4 wt. % sorbitol, preferably 0.01 to 0.2 wt. %, preferably 0.01 to 0.1 wt. %, preferably 0.01 to 0.04 wt. %, preferably 0.02 to 0.4 wt. %, preferably 0.02 to 0.02 wt. %, preferably 0.02 to 0.1 wt. %, or preferably 0.02 to 0.04 wt. %, preferably at most 0.4 wt. % sorbitol, preferably at most 0.2 wt. %, preferably at most 0.1 wt. %, or preferably at most 0.04 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain sorbitol.

In a preferred embodiment according to the invention, the 1,1-GPM- and/or 1,6-GPS-enriched isomalt composition according to the invention has 0.01 to 2 wt. % sucrose, preferably 0.01 to 1 wt. %, preferably 0.01 to 0.6 wt. %, preferably 0.01 to 0.4 wt. %, or preferably 0.01 to 0.1 wt. %, preferably at most 2 wt. % sucrose, preferably at most 1 wt. %, preferably at most 0.6 wt. %, preferably at most 0.4 wt. %, or preferably at most 0.1 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain sucrose.

In a preferred embodiment, the 1,1-GPM- and/or 1,6-GPS-enriched isomalt composition according to the invention has 0.1 to 10 wt. % 1,1-GPS, preferably 0.1 to 8 wt. %, preferably 0.1 to 6 wt. %, preferably 0.1 to 4 wt. %, preferably 0.1 to 2 wt. %, preferably 0.1 to 1 wt. %, preferably 0.1 to 0.6 wt. %, preferably 0.1 to 0.4 wt. %, preferably 0.1 to 0.2 wt. %, preferably 0.2 to 10 wt. %, preferably 0.2 to 8 wt. %, preferably 0.2 to 6 wt. %, preferably 0.2 to 4 wt. %, preferably 0.2 to 2 wt. %, preferably 0.2 to 1 wt. %, preferably 0.2 to 0.6 wt. %, or preferably 0.2 to 0.4 wt. %, preferably at most 10 wt. % 1,1-GPS, preferably at most 8 wt. %, preferably at most 6 wt. %, preferably at most 4 wt. %, preferably at most 2 wt. %, preferably at most 1 wt. %, preferably at most 0.6 wt. %, preferably at most 0.4 wt. %, or preferably at most 0.2 wt. % (each based on the total weight (DM) of the 1,1-GPM- and/or 1,6-GPS-enriched isomalt composition).

In a particularly preferred embodiment according to the invention, the 1,1-GPM- and/or 1,6-GPS-enriched isomalt composition according to the invention does not contain 1,1-GPS.

In a preferred embodiment according to the invention, the 1,1-GPM- and/or 1,6-GPS-enriched isomalt composition according to the invention has 0.01 to 2 wt. % of glycosylglycitols, preferably 0.01 to 1 wt. %, preferably 0.01 to 0.6 wt. %, preferably 0.01 to 0.4 wt. %, preferably 0.01 to 0.1 wt. %, preferably 0.03 to 2 wt. %, preferably 0.03 to 1 wt. %, preferably 0.03 to 0.6 wt. %, preferably 0.03 to 0.4 wt. %, preferably 0.03 to 0.1 wt. %, or preferably 0.03 to 0.1 wt. %, preferably at most 2 wt. % glycosylglycitols, preferably at most 0.6 wt. %, preferably at most 0.4 wt. %, or preferably at most 0.1 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain glycosylglycitols.

In a preferred embodiment, the 1,1-GPM- and/or 1,6-GPS-enriched isomalt composition according to the invention has from 0.01 to 2 wt. % of deoxy-disaccharide alcohols, preferably from 0.01 to 1 wt. %, preferably 0.01 to 0.6 wt. %, preferably 0.01 to 0.2 wt. %, preferably 0.01 to 0.1 wt. %, preferably 0.03 to 2 wt. %, preferably 0.03 to 1 wt. %, preferably 0.03 to 0.6 wt. %, preferably 0.03 to 0.2 wt. %, or preferably 0.03 to 0.1 wt. %, preferably at most 2 wt. % of deoxy-disaccharide alcohols, preferably at most 1 wt. %, preferably at most 0.6 wt. %, preferably at most 0.2 wt. %, or preferably at most 0.1 wt. % (each based on the total weight (DM) of the 1,1-GPM- and/or 1,6-GPS-enriched isomalt composition).

In a particularly preferred embodiment according to the invention, the 1,1-GPM- and/or 1,6-GPS-enriched isomalt composition according to the invention does not contain deoxy-disaccharide alcohols. In a preferred embodiment according to the invention, the 1,1-GPM- and/or 1,6-GPS-enriched isomalt composition according to the invention has 0.01 to 2 wt. % GPI, preferably 0.01 to 1 wt. %, preferably 0.01 to 0.6 wt. %, preferably 0.01 to 0.4 wt. %, or preferably 0.01 to 0.1 wt. %, preferably at most 2 wt. % GPI, preferably at most 1 wt. %, preferably at most 0.6 wt. %, preferably at most 0.4 wt. %, or preferably at most 0.1 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain GPI.

In a preferred embodiment according to the invention, the 1,1-GPM- and/or 1,6-GPS-enriched isomalt composition according to the invention has from 0.01 to 2 wt. % isomaltose, preferably from 0.01 to 1 wt. %, preferably from 0.01 to 0.6 wt. %, preferably from 0.01 to 0.4 wt. %, or preferably from 0.01 to 0.1 wt. %, preferably at most 2 wt. % GPI, preferably at most 1 wt. %, preferably at most 0.6 wt. %, preferably at most 0.4 wt. %, or preferably at most 0.1 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain isomaltose.

In a preferred embodiment according to the invention, the 1,1-GPM- and/or 1,6-GPS-enriched isomalt composition according to the invention has 0.01 to 2 wt. % isomelecitose, preferably 0.01 to 1 wt. %, preferably 0.01 to 0.6 wt. %, preferably 0.01 to 0.4 wt. %, or preferably 0.01 to 0.1 wt. %, preferably at most 2 wt. % GPI, preferably at most 1 wt. %, preferably at most 0.6 wt. %, preferably at most 0.4 wt. %, or preferably at most 0.1 wt. % (each based on the total weight (DM) of the 1,1-GPM- and/or 1,6-GPS-enriched isomalt composition).

In a preferred embodiment according to the invention, the 1,1-GPM- and/or 1,6-GPS-enriched isomalt composition according to the invention does not contain isomelecitose.

In a preferred embodiment according to the invention, the 1,1-GPM- and/or 1,6-GPS-enriched isomalt composition according to the invention has a particle size distribution according to which at least 90% of the particles have a particle size, in particular a diameter, of 100 to 1000 μm, preferably 100 to 800 μm, preferably 100 to 200 μm, preferably 100 to 500 μm, preferably 200 to 800 μm, preferably 300 to 600 μm, preferably 20 to 80 μm, preferably 40 to 80 μm, or preferably 50 to 100 μm.

In a preferred embodiment according to the present invention, the 1,1-GPM- and/or 1,6-GPS-enriched isomalt composition according to the present invention has a particle size distribution according to which at least 90% of the particles have a particle size, in particular a diameter, of at most 1000 μm, preferably at most 800 μm, preferably at most 600 μm, preferably at most 500 μm, preferably at most 400 μm, preferably at most 200 μm, preferably at most 100 μm, preferably at most 80 μm, preferably at most 40 μm, preferably at most 20 μm.

In a further aspect, the present invention also provides the use of the 1,1-GPM- and/or 1,6-GPS-enriched isomalt compositions produced by the method according to the invention in products for human and/or animal consumption. Preferably, the product for human or animal consumption is a food product or luxury product or a pharmaceutical product.

In a preferred embodiment according to the present invention, the food product or luxury product is a confectionery, a filling for confectionery, a soft caramel, a hard caramel, a fondant, a yoghurt, a biscuit, a chewing gum, an ice cream, milk, a milk product, a beverage, fruit juice, a fruit juice concentrate, a fruit preparation, a jam, a jelly or a smoothie.

In the context of the present invention, the term "isomalt" or "hydrogenated isomaltulose" is preferably understood to mean a mixture consisting of or comprising 1,1-GPM and 1,6-GPS, in particular a mixture consisting of or comprising 35 to 61 wt. % 1,1-GPM and 65 to 39 wt. % 1,6-GPS, in particular an equimolar or nearly equimolar mixture consisting of or comprising 1,1-GPM and 1,6-GPS. Accordingly, isomalt can also be understood as mixtures consisting of or comprising 1,1-GPM and 1,6-GPS which do not have an equimolar ratio of 1,1-GPM to 1,6-GPS but in which there is a higher 1,1-GPM- than 1,6-GPS-content or a higher 1,6-GPS-than 1,1-GPM-content.

In a particularly preferred embodiment, the isomalt has no components other than the two components 1,1-GPM and 1,6-GPS.

In a particularly preferred embodiment, the isomalt has, in addition to the two components 1,1-GPM and 1,6-GPS, one or more further components, for example mannitol, sorbitol, sucrose, 1,1-GPS (1-O-α-D-glucopyranosyl-D-sorbitol), glycosylglycitols, deoxy-disaccharide alcohols, GPI (glucopyranosyl-iditol), isomaltose, isomaltulose, isomelezitose, hydrogenated or non-hydrogenated oligosaccharides, in particular hydrogenated or non-hydrogenated trisaccharides, or/and other compounds.

In the context of the present invention, a 1,1-GPM- and/or 1,6-GPS-enriched isomalt composition obtained according to the invention is preferably understood to be a 1,1-GPM- and/or 1,6-GPS-enriched isomalt, i.e. in the case of a 1,1-GPM-enriched isomalt composition a composition in which a higher 1,1-GPM-than 1,6-GPS-content is present, and in the case of a 1,6-GPS-enriched isomalt composition a composition in which a higher 1,6-GPS-than 1,1-GPM-content is contained.

In the context of the present invention, a 1,1-GPM-enriched phase obtained according to the invention or a 1,1-GPM-enriched isomalt composition obtained according to the invention, is understood to be in particular a phase or a mixture in which at least 57 wt. % 1,1-GPM, preferably at least 60, in particular at least 70, in particular at least 80, in particular at least 90, in particular at least 95, in particular at least 98, in particular at least 99 wt. % 1,1-GPM and at most 43 wt. % 1,6-GPS, in particular at most 40, in particular at most 30, in particular at most 20, in particular at most 10, in particular at most 5, in particular at most 2, in particular at most 1 wt. % 1,6-GPS (each based on the total weight of the dry matter of the amount of 1,6-GPS and 1,1-GPM present in the phase or composition).

In the context of the present invention, a 1,6-GPS-enriched phase obtained according to the invention or a 1,6-GPS-enriched isomalt composition obtained according to the invention is understood to be a phase or a mixture in which at least 57 wt. % 1,6-GPS, preferably at least 60, in particular at least 70, in particular at least 80, in particular at least 90, in particular at least 95, in particular at least 98, in particular at least 99 wt. % 1,6-GPS and at most 43 wt. % 1,1-GPM, in particular at most 40, in particular at most 30, in particular at most 20, in particular at most 10, in particular at most 5, in particular at most 2, in particular at most 1 wt. % 1,1-GPM (each based on the total weight of the dry matter of the amount of 1,1-GPM and 1,6-GPS present in the phase or the composition).

In a preferred embodiment, a 1,1-GPM- and/or 1,6-GPS-enriched isomalt composition may also be a 1,1-GPM- and/or 1,6-GPS-enriched phase. A 1,1-GPM-enriched phase and a 1,1-GPM-enriched isomalt composition obtained according to the invention, in particular according to method step e), has a higher 1,1-GPM-content than the isomalt-containing solution used for its preparation according to the invention, in particular according to method step a). A 1,6-GPS-enriched phase and a 1,6-GPS-enriched composition obtained according to the invention, in particular according to method step e), has a higher 1,6-GPS-content than the isomalt solution used for its preparation according to the invention, in particular according to method step a).

In a preferred manner, the 1,1-GPM-content in the 1,1-GPM-enriched phase or composition, which is higher than in the isomalt-containing solution, is increased by at least 5, at least 10, at least 15, at least 20, at least 30, at least 40, at least 50, at least 60, at least 70, at least 80, at least 90, at least 100, at least 150 and in particular at least 200 wt. % (each based on the 1,1-GPM-content in the isomalt solution provided according to method step a)).

In a preferred manner, the 1,6-GPS-content in the 1,6-GPS-enriched phase or composition, which is higher than in the isomalt-containing solution, is increased by at least 5, at least 10, at least 15, at least 20, at least 30, at least 40, at least 50, at least 60, at least 70, at least 80, at least 90, at least 100, at least 150 and in particular at least 200 wt. % (each based on the 1,6-GPS-content in the isomalt solution provided according to method step a)).

In the context of the present invention, the term "nucleation" is understood to mean crystal nucleation, i.e., the first sub-process that initiates a first-order phase transition. Through crystal nucleation, a new phase, thermodynamically stable under the given conditions, is formed by nuclei from an already present, metastable phase, preferably a supersaturated phase.

In the context of the present invention, the term "supersaturated solution" or "supersaturated phase" is understood to mean a metastable state of a solution which contains a greater amount of a solute than corresponds to the solubility of that solute at a given temperature. Such a supersaturated solution is preferably formed by slow cooling of a saturated solution, by evaporation of part of the solvent, or by a combination of cooling of the saturated solution and evaporation of part of the solvent before the excess solute precipitates, in particular crystallises.

In the context of the present invention, the term "flash evaporation" is understood to mean flash evaporation, i.e., the generation of vapour when the pressure in a reactor filled with liquid is lowered. Flash evaporation produces an increase in supersaturation of the isomalt-containing solution, which, in combination with the shear forces acting on the solution, leads to nucleation. In a flash evaporator, vapour is generated when the pressure in a reactor filled with liquid is lowered, especially as the liquid enters the reactor superheated during flash evaporation. The energy transfer induced in this way leads to a cooling of the solution, especially the supersaturated solution, with a simultaneous increase in the dry matter content whereby nucleation occurs. Flash evaporation occurs in a reactor filled with saturated or supersaturated liquid and associated vapour phase when the pressure is reduced.

Preferably according to the invention, flash evaporation can be carried out continuously or discontinuously. In an according to the present invention preferably conducted continuous flash evaporation, an isomalt-containing solution is continuously fed to the reactor with simultaneous discharge of the crystal syrup suspension according to the present invention obtained by flash evaporation.

In the context of the present invention, the term "isothermal crystallisation" is understood to mean crystallisation of a solution or suspension which is maintained at a constant crystallisation temperature until crystallisation is complete or until a certain amount of a component, in particular a 1,1-GPM-enriched crystalline phase or a 1,6-GPS-enriched crystalline phase, has crystallised out of the solution or suspension.

In the context of the present invention, a 1,1-GPM-enriched or a 1,6-GPS-enriched phase is understood to mean in each case a 1,1-GPM-enriched or a 1,6-GPS-enriched isomalt composition of similar physical and chemical properties, for example a liquid or crystalline phase. Accordingly, such a phase has at least each of a 1,1-GPM-enriched and/or 1,6-GPS-enriched isomalt composition, optionally together with one or more solvents.

In the context of the present invention, a "multiple-effect evaporator" is understood to be an evaporator in which a solution or suspension is crystallised in multiple stages at low temperatures. In a multiple-effect evaporator, a solution is brought to boiling in several stages in a row, wherein each of the successive reactors has a lower pressure than the previous one. As a result of the lowering pressure in the series of reactors connected in series, the boiling point of the solvent in the series of reactors connected in series successively decreases.

In the context of the present invention, the term "cooling crystallisation" is understood to mean crystallising a compound out of a solution or suspension by lowering the temperature until crystallisation is complete or until a certain amount of a component, in particular a 1,1-GPM-enriched crystalline phase or a 1,6-GPS-enriched crystalline phase, has crystallised out of the solution or suspension.

In the context of the present invention, the term "multi-stage evaporative crystallisation" is understood to mean the enrichment of a crystalline phase by crystallisation in multiple reactors, each with different pressure levels and/or temperatures.

In the context of the present invention, a "phase" is understood to be a contiguous or non-contiguous spatial portion of the suspension in which homogeneous substantially equal material properties are present. A liquid phase is therefore that portion of the suspension which is characterised by its liquid state of aggregation. A crystalline phase is that portion of the suspension which is characterised by its crystalline and thus solid state of aggregation.

In the context of the present invention, a "crystalline phase" or a "liquid phase" is understood to be a phase which is formed in the course of the method according to method steps b) and c).

In the context of the present invention, a "reduced or lowered" absolute pressure is understood to be an absolute pressure which is reduced compared to the absolute ambient pressure, in particular the atmospheric pressure of 1 bar.

In the context of the present invention, unless otherwise stated and/or apparent, the percentages of individual components indicated for a composition of components add up to 100 wt. %, that is, the total composition.

In the context of the present invention, the term "and/or" is understood to mean that all members of a group which are attached by the term "and/or" are represented both cumulatively with each other in any combination, and alternatively with each other. By way of example, for the expression "A, B and/or C", the following disclosure is to be understood thereunder: i) (A or B or C), or ii) (A and B), or iii) (A and C), or iv) (B and C), or v) (A and B and C).

In the context of the present invention, "shear" is understood to mean a mechanical agitation, that is preferably a movement, in particular an agitation.

In the context of the present invention, "agitator" is understood to mean in particular a rotor-stator system.

In the context of the present invention, "rotor-stator system" is particularly understood to mean a homogeniser.

In the context of the present invention, "rotor" is understood to mean the rotating part of a homogeniser, in particular where a stator is present.

In the context of the present invention, "stator" is understood to mean the immovable part of a homogeniser, in particular when a rotor is present.

In the context of the present invention, the rotor is a propeller stirrer present in the stator, a central tube, and capable of rotating in the central tube.

In the context of the present invention, "a rotor blade having a rectangular shape" is understood to mean a rotor blade having a constant blade depth.

In the context of the present invention, "a rotor blade with a trapezoidal shape" is understood to mean a rotor blade that has a decreasing blade depth along its length.

In the context of the present invention, "a rotor blade with a double trapezoidal shape" is understood to mean a rotor blade that has a blade depth that increases and then decreases along its length.

In the context of the present invention, "a rotor blade with a rectangular trapezoidal shape" is understood to mean a rotor blade that has a blade depth that is constant along its length and then decreases.

In the context of the present invention, "crystal" is understood to mean a solid body with building blocks, in particular molecules, arranged regularly in a crystal structure.

In the context of the present invention, "reactor" is understood to mean a container, in particular a container, in particular a ripening container, in which method step b) and/or method step c) is particularly preferably carried out.

In the context of the present invention, "evaporation" is understood to mean the transition of a liquid or a liquid mixture into the gaseous aggregate state.

In the context of the present invention, "reverse osmosis" is understood to mean the reverse principle of osmosis, wherein osmosis describes the process of equalising the concentration of two liquids through a semi-permeable membrane. Reverse osmosis preferably takes place at a pressure higher than atmospheric pressure. As a result, the dissolved compound, in particular isomalt, remains in the initial solution or suspension and the solvent, in particular water, is removed through the solvent-permeable, in particular water-permeable membrane.

In the context of the present invention, "inoculation" is understood to mean the addition of seed crystals to the solution or suspension to be inoculated.

In the context of the present invention, "blade tip speed" is also understood to mean rotor blade tip speed, which is measured at the tip, i.e., the outer end of the rotor blade.

In the context of the present invention, the length-to-width ratio of crystals is determined according to the methodology described in Example 2.

Further advantageous embodiments of the invention will be apparent from the subclaims.

The invention will be explained in more detail with reference to embodiment examples and comparative examples and associated figures.

The Figures Show:

FIG. 1: Solubility diagram according to Schiweck (H. Schiweck, alimenta 19, Palatinit®-Herstellung, technologische Eigenschaften und Analytik palatinithalthaltiger Lebensmittel, 5-16, 1980) for 1,1-GPM (GPM, 3), 1,6-GPS (GPS, 2) and isomalt (Isomalt, 1) in water, in which the solubility limits of the above-mentioned components are shown as a function of temperature, FIG. 2A to 2D: Microscopic images of crystallisation products from example 2.1 (magnification ×4), FIG. 3A to 3D: Microscopic images of crystallisation products from example 2.1 (magnification ×10), FIG. 4A to 4D: Microscopic images of crystallisation products from example 2.2 (magnification ×10 and ×20), FIG. 5A to 5F: Microscopic images of crystallisation products from example 2.3 (magnification ×4 and ×10), FIG. 6A to 6F: Microscopic images of crystallisation products from example 2.4 (magnification ×4 and ×10),

Example 1

Separation of isomalt (hydrogenated isomaltulose) into 1,1-GPM- and 1,6-GPS-enriched isomalt compositions by flash evaporation in method step b) and subsequent isothermal crystallisation in method step c).

The two main components of isomalt, i.e., 1,1-GPM and 1,6-GPS, have different solubility products in aqueous solutions (FIG. 1). In suspension, each component forms its own solubility equilibrium. The more easily crystallising or poorly soluble component 1,1-GPM accumulates in the solid part of the suspension (crystalline phase), since the less easily crystallising or more soluble component 1,6-GPS preferentially goes into solution or remains in solution. The equilibria that form are temperature-dependent for the same concentration of isomalt in water in the suspension. At the same temperature, the proportion of 1,6-GPS in the solution increases as the proportion of the dry matter (DM) in the suspension increases. The solubility diagram of 1,1-GPM, 1,6-GPS and isomalt (Figure) shows a steady increase in the solubility of each component with increasing temperature. The present invention makes use of this observation. An isomalt-containing solution obtained by conventional process steps is thermally thickened in a method step a1) to a dry matter content of 70 to 85 wt. %. The isomalt-containing solution thus obtained and provided in method step a) (isomalt content 70 to 85 wt. % based on the total weight of the solution) with a content of 1,1-GPM of 35 to 44 wt. %, namely 40.7 wt. %, and a content of 1,6-GPS of 56 to 65 wt. %, namely 58.4 wt. %, 0.01 to 2 wt. % GPI, 0.01 to 2 wt. % glycosylglycitols, 0.01 to 0.4 wt. % sorbitol, 0.001 to 2 wt. % deoxy-disaccharide alcohols, 0.1 to 10 wt. % 1,1-GPS and/or 0.01 to 0.3 wt. % mannitol (each based on the total weight of the dry matter of the isomalt-containing solution) is then brought to a temperature of 60 to 75° C. and then subjected to flash evaporation according to method step b) of the method according to the invention for crystal nucleation in the so-called nucleator. After adjusting the temperature of the isomalt-containing solution to 60 to 75° C., the flash evaporation is operated at an absolute pressure of 50 to 200 mbar, in particular 90 to 100 mbar, and at a temperature of 50 to 55° C. Due to the reduced absolute pressure, the vapour pressure increases and the induced energy dissipation causes the 1,1-GPM, which is less soluble in water than 1,6-GPS (see solubility according to Schiweck, FIG. 1), to change into a crystalline first phase according to its thermodynamic solubility product (initially about 5% of the 1,1-GPM present in the initial solution). Due to the agitator geometry used in the reactor and the shear forces thus continuously generated, further 1,1-GPM-enriched crystal nuclei are continuously formed.

After a residence time of up to 5 h, about 25 wt. % of the 1,1-GPM initially present in the initial solution has passed into the first crystalline phase, wherein the first liquid phase obtained after carrying out the nucleation process according to method step b) has 31 wt. % 1,1-GPM and 68 wt. % 1,6-GPS (based on the total weight of the dry matter in solution). The first isomalt-containing suspension obtained from method step b), comprising 1,1-GPM-enriched crystal nuclei obtained by method step b), is continuously subjected to a crystallisation process according to method step c), carried out in a temperature-controlled crystalliser. In this process, the 1,1-GPM-enriched crystal nuclei continue to grow into crystals under isothermal conditions in a temperature range of 50 to 60° C., in particular 56° C., until the residual supersaturation has largely dissipated. The obtaining of isothermal conditions is ensured by the continuous removal of the released crystallisation energy. By slowly lowering the temperature of the ripening container (crystalliser) step by step (at most 0.5 K/h, in particular at most 0.1 K/h) to 55° C., the yield of 1,1-GPM-enriched crystals is additionally increased without negatively affecting the purity of these crystals. The second suspension thus obtained can be worked up by means of suitable separation techniques according to method step d) (for example centrifugation), wherein the second crystalline phase thus obtained contains 69.9 wt. % 1,1-GPM and 29.8 wt. % 1,6-GPS (based on the total weight of the dry matter of the second crystalline phase) and the separated second liquid phase contains 20.2 wt. % 1,1-GPM and 78.6 wt. % 1,6-GPS (based on the total weight of the dry matter of the second liquid phase).

Example 2

In the following example, the method according to the invention (Example 2.1) is compared with known crystallisation methods (Examples 2.2 to 2.4).

The experiments were carried out in a 2-litre cooling crystalliser. This is equipped with an agitator and a double jacket for heating by means of a thermostat. The separation of crystal magmas took place in a heated pressure Nutche or in a pilot plant centrifuge. A microscope was used for image documentation of the crystals in the crystal suspensions. The Olympus Stream Motion software was used for image analysis.

The enriched phases obtained from the experiments were analysed as follows:

Analysis of the water content of the filter cake (second crystalline phase) using the Karl Fischer method.

analysis of the water content of the filtrate (second liquid phase) by refractometry Analysis of the 1,1-GPM-content and 1,6-GPS-content by HPLC Analysis of the length-to-width ratio:

Using an Olympus camera (Olympus UC 90) and associated Olympus software and a Zeiss microscope (Carl Zeiss Axiolab re), microscopic crystal images were taken of the glycerol-dispersed second isomalt-containing suspension (Magma) at magnifications of 4× and 10×. At least twenty individual crystals per crystal image, selected by means of a random generator, were measured with regard to crystal length and crystal width using the image analysis software Olympus Stream Motion (maximum characteristic crystal length and, in addition, the maximum characteristic crystal width at a 90° angle) and the ratio of measured length to measured width was determined by calculation and the mean or median value was determined from this. Preferably, a diagonal line laid through the microscopic crystal photo (crystal image) is used as a random generator and all crystals on this diagonal line allowing a clear distinction and determination of the crystal length and width are used for the determination of the length-to-width ratio, wherein at least twenty crystals must be recognisable on the line. Otherwise, another microscopic image was taken and used.

In the following Table 1, the 1,1-GPM- and 1,6-GPS-contents of the isomalt solutions used in this example are given in relation to DM (dry matter) and total mass of the isomalt solution).

TABLE 1

Analysis of the initial isomalt solutions

| | 1,1-GPM-content in g/100 gDS | 1,6-GPS-content in g/100 gDS | 1,1-GPM-content in g/100 g | 1,6-GPS-content in g/100 g |
|---|---|---|---|---|
| Example 2-1 | 40.40 | 57.39 | 31.4 | 44.6 |
| Example 2-2 | 46.08 | 51.39 | 22.6 | 25.2 |
| Example 2-3 | 46.63 | 51.00 | 36.2 | 39.6 |
| Example 2-4 | 46.66 | 51.30 | 36.2 | 39.8 |

Example 2.1 (According to the Invention)

A second suspension (magma) obtained according to the teaching of example 1 is partially removed from the crystallizer before centrifugation according to method step d), diluted in glycerol and crystal images are recorded. Further, a separation according to method step d) of the solid from the liquid phase is carried out in a centrifuge at a speed of 1800 revolutions per minute for 30 minutes:

FIGS. 2A to 2D show crystal images of the obtained magma dispersed in glycerol, magnification ×4, and FIGS. 3A to 3D show crystal images of the obtained magma dispersed in glycerol, magnification ×10.

The length-to-width ratio of the crystals obtained in the magma and in the second crystalline phase obtained in method step d) were 8.0 (mean) and 7.8 (median).

Table 2 below shows the composition of the phases obtained after separation (filter cake is the solid crystalline phase, filtrate is the liquid phase).

TABLE 2

| Analysis of the enriched phases, each based on total mass | | |
|---|---|---|
| | Filter cake | filtrate |
| Water content in g/100 g | 16.1 | 25.9 |
| 1,1-GPM-content in g/100 g | 55.2 | 15.3 |
| 1,6-GPS-content in g/100 g | 29.4 | 56.8 |
| Ratio of 1,1-GPM to 1,6-GPS in g/g | 1.88 | 0.27 |
| 1,1-GPM-content in g/100 gDS | 65.8 | 20.6 |
| 1,6-GPS-content in g/100 gDS | 35.0 | 76.6 |

The obtained crystals in the solid phase are particularly pure and show a high uniformity in shape and size. The crystal suspension after completion of crystallisation shows no fine grain formation in the crystal image. The length-to-width ratio of the crystals contained in the second crystalline phase obtained in method step d) is comparatively small. The separation of the obtained second crystalline phase by centrifugation was took place without problems in a very satisfactory manner, which is particularly shown in the enrichment of 1,1-GPM in the crystalline phase after centrifugation. The 1,6-GPS-enriched filtrate, i.e., the 1,6-GPS-enriched second liquid phase, drains very well from the filter cake. According to the invention, an enrichment of 1,1-GPM and a depletion of 1,6-GPS are found in the obtained second crystalline phase, while similarly, an enrichment of 1,6-GPS and a depletion of 1,1-GPM are found in the obtained second liquid 1,6-GPS-enriched phase, each compared to the starting composition.

Example 2.2 (not According to the Invention)

WO 1997/008958 A1 discloses methods for producing 1,6-GPS-enriched and 1,1-GPM-enriched mixtures. Example 2 of this document discloses the preparation of 1,1-GPM and 1,6-GPS-enriched 1,1-GPM/1,6-GPS mixtures, wherein Isomalt$^R$ is added to 5 kg of water (fully demineralised) and the obtained suspension is stirred at 35° C. for 1-20 hours depending on the particle size. Subsequently, this suspension is separated into a liquid phase and solid phase at 35° C. in a heated pressure Nutsche.

Experimental Procedure:

1. switch on the thermostat for heating the 2-litre crystalliser adjust the flow temperature to 35.3° C. Temperature control via the internal temperature sensor of the thermostat.
2. add 999.79 g of demineralised water to the 2-litre crystalliser
3. switch on the stirrer and adjust the speed to 60 rpm
4. preheat the water to 35° C.
5. add 999.96 g Isomalt ST-M to the 2-litre crystalliser
6. 19.5 hours after addition of the Isomalt: Preheat the double-jacket pressure Nutsche to 35° C. via thermostat
7. 20 hours after addition of the isomalt: Removal of the obtained crystal suspension (magma) from the crystalliser
8. produce a dilution of part of the magma with demineralised water (one to one) for analysis
9. disperse a part of the magma in glycerine for recording crystal images in the suspension
10. transfer 200 ml of magma into the preheated pressure Nutsche and separate the crystal from the mother solution. A filter fleece made of polyethylene of the company Porvair Sciences type Vyon D with a mesh size of 15-25 μm is used as a filter.
11. dilution of the collected filtrate with demineralised water (one to one) for analysis
12. removal of crystals from the pressure Nutsche for analysis Experimental Results:

According to example 2 of WO 1997/008958 A1, no isomalt-containing solution but a suspension of isomalt in water is used as starting material for the desired enrichments and subsequent separation of the enriched solid and liquid phases. Therefore, no crystallisation of isomalt components from a solution takes place in this method during the incubation at 35° C. for about 20 hours, but only a partial solving and dissolving of undissolved isomalt components from the solid phase of the suspension into the liquid phase and vice versa.

FIGS. 4A and 4B show images of the obtained magma dispersed in glycerol, magnification ×10, and FIGS. 4C and 4D show images of the obtained magma dispersed in glycerol, magnification ×20.

Despite the chosen high-resolution magnification, no single crystals are visible, but only partially dissolved, flake-like particles, which is due to the partially amorphous solidified structure of the isomalt particles used in the initial suspension, which represent conglomerates of small crystallites of 1,1-GPM and 1,6-GPS. These do not originate from a crystallisation process but from a drying process and consequently do not show any crystal forms to be expected in a classical crystallisation. The principle of enrichment realised in this comparative example is based on a release of the more soluble 1,6-GPS component from a solid containing 1,1-GPM and 1,6-GPS 20 and thus does not correspond to an enrichment according to the invention by crystallisation from a solution containing 1,1-GPM and 1,6-GPS.

Table 3 below shows the 1,1-GPM- and 1,6-GPS-contents of the phases obtained after separation.

TABLE 3

| Analysis of the enriched phases (filter cake is the solid crystalline phase, filtrate is the liquid phase), each based on total mass | | |
|---|---|---|
| | Filter cake | filtrate |
| Water content in g/100 g | 21.2 | 55.4 |
| 1,1-GPM-content in g/100 g | 69.0 | 15.1 |
| 1,6-GPS-content in g/100 g | 9.6 | 28.0 |
| Ratio of 1,1-GPM to 1,6-GPS in g/g | 7.22 | 0.54 |
| 1,1-GPM-content in g/100 gDS | 87.6 | 33.9 |
| 1,6-GPS-content in g/100 gDS | 12.1 | 62.8 |

Example 2.3 (not According to the Invention)

EP 0859 006 B2 discloses methods for producing 1,6-GPS-enriched and 1,1-GPM-enriched mixtures. Example 1 of this document discloses the production of 1,1-GPM and 1,6-GPS-enriched 1,1-GPM/1,6-GPS mixtures using a seeding step and two different cooling rates during crystallisation.

Experimental Procedure:

1. switch on the thermostat to heat the 2-litre crystalliser and adjust the feed temperature to 85° C.
2. add 649.91 g demineralised water to the 2-litre crystalliser
3. switch on the stirrer and adjust the speed to 100 rpm
4. heat the water to 85° C.
5. add 2453.2 g Isomalt ST-F to the 2-litre crystalliser
6. start the cooling program a. Maintain 85° C. for 2 hours—temperature control via external PT100 in the crystalliser—stirrer speed 100 rpm
b. cool 85° C. to 65° C. for 2 hours—temperature control via internal PT100 in the thermostat—stirrer speed 60 rpm
c. cool 65° C. to 37° C. over 23.3 hours—temperature control via internal PT100 in thermostat—stirrer speed 60 rpm
7. after reaching 62° C.: add 0.5 g Isomalt ST-PF in 4.95 g isopropanol to the solution via a syringe
8. after reaching 37° C.: removal of the magma from the crystalliser
9. produce a dilution of part of the magma with demineralised water (one to one) for analysis
10. disperse a part of the magma in glycerine to record crystal images in the suspension
11. transfer 604 g of magma into a centrifuge and separate the crystal and mother solution. The sieve used is a filter fleece made of polyethylene from Porvair Sciences type Vyon D with a mesh size of 15-25 μm. Speed is 1800 revolutions per minute. Centrifugation time 30 minutes. No water cover.
12. dilution of the collected outlet with demineralised water (one to one) for analysis
13. removal of the crystals from the centrifuge Separation in the centrifuge could not be carried out satisfactorily. The mass of outlet was low. The filter cake had a visually clearly recognisable high residual moisture.

FIGS. 5A, 5B and 5C show crystal images, magma dispersed in glycerol, magnification ×4, and FIGS. 5D, 5E and 5F crystal images, magma dispersed in glycerol, magnification ×10.

The length-to-width ratio of the crystals in the magma 11.2 (mean) and 11.1 (median).

Table 4 below shows the 1,1-GPM- and 1,6-GPS-contents of the phases obtained after separation.

TABLE 4

Analysis of the enriched phases (filter cake is the solid crystalline phase, filtrate is the liquid phase), each based on total mass

| | Filter cake | filtrate |
|---|---|---|
| Water content in g/100 g | 19.0 | 30.2 |
| 1,1-GPM-content in g/100 g | 42.9 | 11.3 |
| 1,6-GPS- content in g/100 g | 35.6 | 56.0 |
| Ratio of 1,1-GPM to 1,6-GPS in g/g | 1.21 | 0.20 |
| 1,1-GPM- content in g/100 gDS | 53.0 | 16.3 |
| 1,6-GPS- content in g/100 gDS | 44.0 | 80.3 |

The crystal images clearly show that significant fine grain formation occurs in the crystal suspension after completion of crystallisation. The length-to-width ratio of the crystals is relatively large. Separation of the crystalline phase by centrifugation is not satisfactory. The enrichment of 1,1-GPM in the obtained crystalline phase after centrifugation is minimal and the contents of 1,1-GPM and 1,6-GPS in the filter cake correspond approximately to the composition of the initial solution. The 1,6-GPS-enriched filtrate drains very poorly from the filter cake.

Example 2.4 (not According to the Invention)

U.S. Pat. No. 6,414,138 B1 also discloses methods for producing 1,6-GPS-enriched and 1,1-GPM-enriched mixtures. Example 1 of this document discloses the production of 1,1-GPM and 1,6-GPS-enriched 1,1-GPM/1,6-GPS mixture so as described in Example 2.3, but using two different cooling rates during crystallisation without seeding.

Experimental Procedure:

1. switch on the thermostat to heat the 2-litre crystalliser and adjust the feed temperature to 85° C.
2. add 627.44 g demineralised water to the 2-litre crystalliser
3. switch on the stirrer and adjust the speed to 100 rpm
4. heat the water to 85° C.
5. add 2372.5 g Isomalt ST-F to the 2-litre crystalliser
6. start the cooling programme a. Maintain 85° C. for 2 hours—temperature control via external PT100 in the crystalliser—stirrer speed 100 rpm
b. cool 85° C. to 65° for 2 hours—temperature control via internal PT100 in the thermostat—stirrer speed 60 rpm
c. cool 65° C. to 37° C. g over 23.3 hours—temperature control via internal PT100 in thermostat—stirrer speed 60 rpm 7. after reaching 37° C.: removal of the magma from the crystalliser
8. produce a dilution of part of the magma with demineralised water (one to one) for analysis
9. disperse a part of the magma in glycerine to record crystal images in the suspension FIGS. 6A, 6B and 6C show crystal images, magma dispersed in glycerol, magnification ×4 and FIGS. 6D, 6E and 6F show crystal images, magma dispersed in glycerol, magnification ×10.

The length-to-width ratio of the crystals in the magma was 11.3 (mean) and 10.5 (median).

These crystal images also clearly show that significant fine grain formation occurs in the crystal suspension after completion of crystallisation. The length-to-width ratio of the crystals is relatively large and comparable to that of Example 2.3.

The invention claimed is:

1. A method for producing 1,1-GPM- and/or 1,6-GPS-enriched isomalt compositions from an isomalt-containing solution, characterised in that a) an isomalt-containing solution is provided, wherein the isomalt-containing solution has 65 to 90 wt. % isomalt (based on the total weight of the isomalt-containing solution);
b) the isomalt-containing solution provided in method step a) is subjected to flash evaporation in a reactor for crystal nucleation to obtain a first isomalt-containing suspension comprising a first crystalline phase and a first liquid phase;
c) the first isomalt-containing suspension obtained in method step b) is subjected to a crystallisation process whereby a second isomalt-containing suspension comprising a second crystalline phase and a second liquid phase is obtained, wherein the second crystalline phase is 1,1-GPM-enriched and the second liquid phase is 1,6-GPS-enriched;
d) the 1,1-GPM-enriched second crystalline phase of the second isomalt-containing suspension of method step c) is separated from the 1,6-GPS-enriched second liquid phase; and
e) 1,1-GPM- and/or 1,6-GPS-enriched isomalt compositions are obtained.

2. The method according to claim 1, wherein mechanical agitation is carried out during method step b).

3. The method according to claim 1, wherein the isomalt-containing solution provided in method step a) has 35 to 61 wt. % 1,1-GPM (based on the total weight of the dry matter (DM) of the isomalt-containing solution provided).

4. The method according to claim 1, wherein the isomalt-containing solution provided in method step a) is adjusted to a temperature of 50 to 90° C.

5. The method according to claim 1, wherein the isomalt-containing solution provided in method step a) has 1,1-GPM, 1,6-GPS and at least one compound selected from the group consisting of 1,1-GPS, other deoxy-disaccharide alcohols, polysaccharides, oligosaccharides, trisaccharides, disaccharides, monosaccharides, sorbitol, mannitol and isomelezitose.

6. The method according to claim 1, wherein the isomalt-containing solution provided in method step a) is obtained in method step a1) from an isomalt-containing initial solution or suspension by evaporation or reverse osmosis.

7. The method according to claim 1, wherein the isomalt-containing solution used for method step a1) is obtained by selective hydrogenation.

8. The method according to claim 7, wherein the isomalt-containing solution used for method step a1) is obtained by selective hydrogenation, wherein said selective hydrogenation is 1,6-GPS-selective hydrogenation.

9. The method according to claim 1, wherein the reactor used for flash evaporation in method step b) is a nucleator.

10. The method according to claim 1, wherein the flash evaporation carried out in method step b) is carried out at an absolute pressure of 10 to 500 mbar.

11. The method according to claim 10, wherein the flash evaporation carried out in method step b) is carried out at an absolute pressure of 50 to 200 mbar.

12. The method according to claim 10, wherein the flash evaporation carried out in method step b) is carried out at a temperature of 30 to 70° C.

13. The method according to claim 10, wherein the flash evaporation carried out in method step b) is carried out at a temperature of 30 to 60° C.

14. The method according to claim 1, wherein the flash evaporation carried out in method step b) is carried out over a period of from 2 minutes to 12 hours.

15. The method according to claim 1, wherein the flash evaporation carried out in method step b) is carried out continuously.

16. The method according to claim 1, wherein method step b) is carried out such that during method step b) 20 to 30% of the dissolved 1,1-GPM present in method step a) passes into the first crystalline phase of the first crystalline isomalt-containing suspension (based on the total weight of the dry matter (DM) of 1,1-GPM in the solution provided in method step a)).

17. The method according to claim 1, wherein method step b) is carried out such that during method step b) the dry matter content of the isomalt-containing solution provided in method step a) is increased by 1 to 6 wt. % (each based on the total weight of the dry matter (DM) of the isomalt-containing solution provided and the first isomalt-containing suspension obtained).

18. The method according to claim 1, wherein the crystallisation process according to method step c) is carried out in a crystalliser.

19. The method according to claim 1, wherein the crystallisation process according to method step c) is carried out continuously.

20. The method according to claim 1, wherein the crystallisation process according to method step c) is an isothermal crystallisation.

21. The method according to claim 20, wherein the isothermal crystallisation process according to method step c) is conducted at a temperature of 50 to 60° C.

22. The method according to claim 1, wherein the crystallisation process according to method step c) is a cooling crystallisation.

23. The method according to claim 1, wherein the crystallisation process according to method step c) is an evaporation crystallisation.

24. The method according to claim 23, wherein the evaporation crystallisation process according to method step c) is a multi-stage evaporation crystallisation.

25. The method according to claim 1, wherein no inoculation with seed crystals is carried out during the method.

26. The method according to claim 25, wherein no inoculation with seed crystals is carried out during the isothermal crystallisation in method step c).

27. The method according to claim 1, wherein after method step d) the 1,1-GPM-enriched second crystalline phase is dried and in method step e) a solid 1,1-GPM-enriched isomalt composition is obtained.

28. The method according to claim 1, wherein after method step d) the 1,6-GPS-enriched second liquid phase is concentrated at least once, in particular concentrated to at least 60 wt. % dry matter content (based on the total weight of the second liquid phase), and in method step e) a liquid 1,6-GPS-enriched isomalt composition is obtained.

29. The method according to claim 1, wherein after method step d) the 1,6-GPS-enriched second liquid phase is dried, and in method step e) a solid 1,6-GPS-enriched isomalt composition is obtained.

30. The method according to claim 1, wherein the second crystalline phase separated in method step d) has at least 60 wt. % 1,1-GPM (based on the total weight of the dry matter (DM) of the crystalline phase).

31. The method according to claim 1, wherein the second liquid phase separated in method step d) has at least 72 wt. % 1,6-GPM (based on the total weight of the dry matter (DM) of the second liquid phase).

32. A 1,1-GPM-enriched isomalt composition, produced by a method according to claim 1, wherein the 1,1-GPM-enriched isomalt composition has a length-to-width ratio of the crystals contained therein of from 7.0 to 10.5 (each mean value).

33. A composition for human and/or animal administration, comprising the 1,1-GPM-enriched isomalt composition of claim 32, wherein said composition is a food product or pharmaceutical product.

34. The composition of claim 33, wherein the food product is a confectionary product.

35. The 1,1-GPM-enriched isomalt composition of claim 32, wherein the 1,1-GPM-enriched isomalt composition has a length-to-width ratio of the crystals contained therein of 7.5 to 10.0.

36. The 1,1-GPM-enriched isomalt composition of claim 32, wherein the 1,1-GPM-enriched isomalt composition has a length-to-width ratio of the crystals contained therein of from 7.5 to 9.0.

37. The 1,1-GPM-enriched isomalt composition of claim 32, wherein the 1,1-GPM-enriched isomalt composition has a length-to-width ratio of the crystals contained therein of from 7.5 to 8.5.

38. The 1,1-GPM-enriched isomalt composition of claim 32, wherein the 1,1-GPM-enriched isomalt composition has a length-to-width ratio of the crystals contained therein of from 7.5 to 8.0.

39. A 1,6-GPS-enriched isomalt composition having 1,1-GPM, 1,6-GPS and isomaltulose produced by a method according to claim 1, and wherein said composition has a 1,6-GPS-content of at least 72 wt. % (based on the total weight of the dry matter (DM) of the composition).

40. A composition for human and/or animal administration, comprising the 1,1-GPM- and/or 1,6-GPS-enriched isomalt composition of claim 39, wherein said composition is a food product or pharmaceutical product.

41. The composition of claim 40, wherein the food product is a confectionary product.

* * * * *